US011678911B2

(12) United States Patent
Loch et al.

(10) Patent No.: US 11,678,911 B2
(45) Date of Patent: Jun. 20, 2023

(54) VERTEBRAL FIXATION DEVICES, SYSTEMS, AND METHODS

(71) Applicant: Articular Spine Fix, Inc., Nampa, ID (US)

(72) Inventors: Hartmut Loch, Nampa, ID (US); Paul M. Diperna, Escondido, CA (US); Fred H. Geisler, Petoskey, MI (US)

(73) Assignee: Articular Spine Fix, Inc., Nampa, ID (US)

(*) Notice: Subject to any disclaimer, the term of this patent is extended or adjusted under 35 U.S.C. 154(b) by 399 days.

(21) Appl. No.: 16/581,609

(22) Filed: Sep. 24, 2019

(65) Prior Publication Data

US 2020/0015861 A1 Jan. 16, 2020

Related U.S. Application Data

(63) Continuation of application No. 15/138,076, filed on Apr. 25, 2016, now abandoned.

(60) Provisional application No. 62/152,719, filed on Apr. 24, 2015.

(51) Int. Cl.
*A61B 17/70* (2006.01)

(52) U.S. Cl.
CPC ...... *A61B 17/7047* (2013.01); *A61B 17/7049* (2013.01); *A61B 17/7064* (2013.01); *A61B 17/7076* (2013.01); *A61B 2017/7073* (2013.01)

(58) Field of Classification Search
CPC ............ A61B 17/7047; A61B 17/7049; A61B 17/7064; A61B 17/7076; A61B 2017/7073
See application file for complete search history.

(56) References Cited

U.S. PATENT DOCUMENTS

| 5,522,816 | A | 6/1996 | Dinello et al. | |
| 5,584,832 | A | 12/1996 | Schlaepfer | |
| 5,609,593 | A | 3/1997 | Errico et al. | |
| 7,011,659 | B2 | 3/2006 | Lewis et al. | |
| 7,914,560 | B2* | 3/2011 | Hoy | A61F 2/4405 606/279 |
| 2003/0171750 | A1 | 9/2003 | Chin | |
| 2005/0119748 | A1 | 6/2005 | Reiley et al. | |
| 2005/0131409 | A1 | 6/2005 | Chervitz et al. | |
| 2006/0149239 | A1 | 7/2006 | Winslow et al. | |
| 2007/0055245 | A1* | 3/2007 | Sasso | A61B 17/7064 606/278 |

(Continued)

FOREIGN PATENT DOCUMENTS

| EP | 0558121 A1 * | 2/1993 |
| WO | WO-2014164490 A1 | 10/2014 |
| WO | WO-2016172607 A1 | 10/2016 |

OTHER PUBLICATIONS

PCT/US2016/29016 International Search Report and Written Opinion dated Sep. 30, 2016.

(Continued)

*Primary Examiner* — Eduardo C Robert
*Assistant Examiner* — Tara Rose E Carter
(74) *Attorney, Agent, or Firm* — TraskBritt

(57) ABSTRACT

Described herein is an orthopedic fixation device for use in spinal surgery. The orthopedic device is a pivoting device that comprises one or more hinges. Fixation of multiple vertebrae is accomplished by fixation at the vertebral facet joints. Multiple devices may be further fixed at multiple vertebral levels with the use of a multi-level rod.

21 Claims, 17 Drawing Sheets

(56) References Cited

U.S. PATENT DOCUMENTS

| | | | |
|---|---|---|---|
| 2007/0250166 A1* | 10/2007 | McKay | A61B 17/7064 |
| | | | 623/17.11 |
| 2010/0144694 A1 | 6/2010 | Nakashima et al. | |
| 2010/0160970 A1 | 6/2010 | Sevrain | |
| 2011/0137353 A1 | 6/2011 | Buttermann | |
| 2011/0144694 A1* | 6/2011 | Laeng | A61B 17/7037 |
| | | | 606/263 |
| 2012/0016420 A1 | 1/2012 | Naraghi | |
| 2017/0020577 A1 | 1/2017 | Loch et al. | |

OTHER PUBLICATIONS

U.S. Appl. No. 15/138,076 Office Action dated Mar. 29, 2019.
U.S. Appl. No. 15/138,076 Office Action dated Oct. 6, 2017.
U.S. Appl. No. 15/138,076 Office Action dated Sep. 7, 2018.

* cited by examiner 1116
1112
1118
1120

VERTEBRAL FIXATION DEVICES, SYSTEMS, AND METHODS

CROSS REFERENCE

This application is a continuation of U.S. application Ser. No. 15/138,076, filed Apr. 25, 2016, which claims the benefit of U.S. Provisional Application No. 62/152,719, filed Apr. 24, 2015, each of which are incorporated herein by reference in their entirety.

BACKGROUND

Intervertebral disc disease and disc erosion as well as vertebral disease and vertebral deformity can cause severe back pain. Typically, one of these aforementioned spinal abnormalities leads to a compression of a spinal nerve, which causes back pain that may radiate along the enervation distribution of the affected spinal nerve.

For example, the erosion of an intervertebral disc positioned between two vertebral bodies can lead to a vertebral body collapsing onto the vertebral body directly below it. The collapse of the first vertebral body onto the second vertebral body deforms the vertebral anatomy, which can lead to a compression or pinching of a spinal nerve. The compression or pinching of a spinal nerve typically causes severe radiating pain down the distribution of the compressed or pinched nerve.

A typical surgical treatment for a compressed or pinched spinal nerve is a spinal fusion procedure. A spinal fusion procedure fuses two or more vertebra together to eliminate the motion of these vertebrae, thus alleviating the nerve compression due to abnormal motion of the vertebrae. A typical way to perform the spinal fusion procedure is by placing pedicle screws through the vertebral pedicles and into the vertebral body of two or more collapsed vertebrae, and then attaching supporting bars to the pedicle screws. The supporting bars attached to the placed screws function similarly to scaffolding, connecting and fixing vertebrae together by fixing together pedicle screws embedded in the vertebrae and allowing the vertebrae to be fixed together in a position that approaches the normal anatomic position and does not further move.

SUMMARY

The traditional spinal fusion procedure is invasive and error prone with a risk of spinal nerve injury or compression. A less invasive system or device that minimizes the risk of spinal nerve injury, to be used in spinal or vertebral fusion procedures, would be highly beneficial.

Provided herein is a surgical device. The device comprises a hinge, a first pivoting arm extending from the hinge, wherein the first pivoting arm comprises a first opening in a proximal portion of the first pivoting arm, and a second pivoting arm extending from the hinge, wherein the second pivoting arm comprises a second opening in a proximal portion of the second pivoting arm. The second opening may be substantially aligned with the first opening. The device further comprises a facet rod sized to fit simultaneously through the first opening and the second opening, wherein the facet rod comprises a substantially straight rod. The device further comprises a concave segment coupled with at least one of a first distal portion of the first pivoting arm and a second distal portion of the second pivoting arm.

In an embodiment, at least one of the opening in the proximal portion of the first pivoting arm and the opening in the proximal portion of the second pivoting arm comprises an oblong shape. In an embodiment, the device comprises a retaining element positioned on at least one of a surface of the proximal portion of the first pivoting arm and on a surface of the proximal portion of the second pivoting arm. In an embodiment, the retaining element comprises a penetrating protrusion on at least one of the surface of the proximal portion of the first pivoting arm and the surface of the proximal portion of the second pivoting arm. In an embodiment, the penetrating protrusion comprises a sharp tooth. In an embodiment, the retaining element comprises at least one of a knurled surface and a splined surface. In an embodiment, the concave segment is serrated. In an embodiment, the hinge comprises a hinge rod that passes through a column, the column comprising at least two stacked loops, wherein a first loop is positioned on the distal end of the first pivoting arm and a second loop is positioned on a distal end of the second pivoting arm. In an embodiment, the first pivoting arm comprises a concave shape that curves towards a midline of the device, and the second pivoting arm comprises a concave shape that curves towards the midline of the device. In an embodiment, the facet rod is threaded. In an embodiment, the concave segment is configured to couple with a multi-level rod. In an embodiment, the hinge couples with the first pivoting arm and the second pivoting arm.

Also provided herein is a surgical device comprising a first hinge, a second hinge, and a third hinge. The third hinge is positioned distal to the first and the second hinges. The device further comprises a first pivoting arm extending from the third hinge, wherein the first pivoting arm comprises the first hinge, and a second pivoting arm extending from the third hinge, wherein the second pivoting arm comprises the second hinge. The device further comprises a concave segment coupled with at least one of a first distal portion of the first pivoting arm and a second distal portion of the second pivoting arm. The concave segment is positioned between the third hinge and the first and the second hinges. In an embodiment, the surgical device comprises an opening in a proximal portion of the first pivoting arm and an opening in a proximal portion of the second pivoting arm. In an embodiment, at least one of the opening in the proximal portion of the first pivoting arm and the opening in the proximal portion of the second pivoting arm comprises an oblong shape. In an embodiment, the surgical device comprises a retaining element positioned on at least one of a surface of the proximal portion of the first pivoting arm and on a surface of the proximal portion of the second pivoting arm. In an embodiment, the retaining element comprises a penetrating protrusion on at least one of the surface of the proximal portion of the first pivoting arm and the surface of the proximal portion of the second pivoting arm. In an embodiment, the penetrating protrusion comprises a sharp tooth. In an embodiment, the retaining element comprises at least one of a knurled surface and a splined surface. In an embodiment, the concave segment is serrated. In an embodiment, the hinge comprises a hinge rod that passes through a column, the column comprising at least two stacked loops, wherein a first loop is positioned on the distal end of the first pivoting arm and a second loop is positioned on a distal end of the second pivoting arm. In an embodiment, the first pivoting arm comprises a concave shape that curves towards a midline of the device, and the second pivoting arm comprises a concave shape that curves towards the midline of the device. In an embodiment, the concave segment is configured to couple with a multi-level rod. In an embodiment, the third hinge couples with the first pivoting arm and the second pivoting arm.

Also provided herein is a surgical device comprising a hinge, a first pivoting arm extending from the hinge, a second pivoting arm extending from the hinge, a first concave segment rotatably coupled to the first pivoting arm; and a second concave segment rotatably coupled to the second pivoting arm. In an embodiment, the device comprises an opening in a proximal portion of the first pivoting arm and an opening in a proximal portion of the second pivoting arm.

In an embodiment, at least one of the opening in the proximal portion of the first pivoting arm and the opening in the proximal portion of the second pivoting arm comprises an oblong shape. In an embodiment, the device comprises a retaining element positioned on at least one of a surface of the proximal portion of the first pivoting arm and on a surface of the proximal portion of the second pivoting arm. In an embodiment, the retaining element comprises a penetrating protrusion on at least one of the surface of the proximal portion of the first pivoting arm and the surface of the proximal portion of the second pivoting arm. In an embodiment, the penetrating protrusion comprises a sharp tooth. In an embodiment, the retaining element comprises at least one of a knurled surface and a splined surface. In an embodiment, the concave segment is serrated. In an embodiment, the hinge comprises a hinge rod that passes through a column, the column comprising at least two stacked loops, wherein a first loop is positioned on the distal end of the first pivoting arm and a second loop is positioned on a distal end of the second pivoting arm. In an embodiment, the first pivoting arm comprises a concave shape that curves towards a midline of the device, and the second pivoting arm comprises a concave shape that curves towards the midline of the device. In an embodiment, the first and the second concave segments are configured to couple with a multi-level rod. In an embodiment, the hinge couples with the first pivoting arm and the second pivoting arm.

Also provided herein is a surgical system for fixing multiple vertebrae. The surgical device comprises a first surgical device comprising a first hinge, wherein a first pivoting arm extends from the first hinge, the first pivoting arm comprising a first opening in a proximal portion of the first pivoting arm, and a second pivoting arm extending from the first hinge, wherein the second pivoting arm comprising a second opening in a proximal portion of the second pivoting arm. The second opening is substantially aligned with the first opening. The system further comprises a first concave segment coupled to at least one of the first pivoting arm and the second pivoting arm, and a first facet rod sized to fit simultaneously through the first opening and the second opening, wherein the facet rod comprising a substantially straight rod. The system further comprises a second surgical device comprising a second hinge, wherein a third pivoting arm extends from the second hinge, wherein the third pivoting arm comprises a third opening in a proximal portion of the third pivoting arm, and a fourth pivoting arm extending from the second hinge. The system comprises a second concave segment coupled to at least one of the first pivoting arm and the second pivoting arm, a second facet rod sized to fit simultaneously through the third opening and the fourth opening, the facet rod comprising a substantially straight rod, and a multi-level rod coupled to the first and second surgical devices.

In an embodiment, at least one of the first opening, the second opening, the third opening, and the fourth opening comprise and oblong shape. In an embodiment, the surgical device comprises a retaining element positioned on at least one of a surface of the proximal portion of the first pivoting arm and on a surface of the proximal portion of the second pivoting arm. In an embodiment, the retaining element comprises a penetrating protrusion on at least one of the surface of the proximal portion of the first pivoting arm and the surface of the proximal portion of the second pivoting arm. In an embodiment, the penetrating protrusion comprises a sharp tooth. In an embodiment, the retaining element comprises at least one of a knurled surface and a splined surface. In an embodiment, the concave segment is serrated. In an embodiment, the hinge comprises a hinge rod that passes through a column, the column comprising at least two stacked loops, wherein a first loop is positioned on the distal end of the first pivoting arm and a second loop is positioned on a distal end of the second pivoting arm. In an embodiment, the first and the second pivoting arm comprises a concave shape that curves towards a midline of the first device. In an embodiment, the third and fourth pivoting arm comprises a concave shape that curves towards a midline of the second device. In an embodiment, the multi-level rod is sized to the space between two vertebral facet joints on the ipsilateral side of two contiguous vertebrae. In an embodiment, the concave segment is configured to couple with a multi-level rod. In an embodiment, the hinge couples with the first pivoting arm and the second pivoting arm.

Also provided herein is a method for fixing a surgical device to a vertebral facet joint comprising receiving a surgical device comprising a hinge, a first pivoting arm extending from the hinge, and a second pivoting arm extending from the hinge. A first opening is in a proximal portion of the first pivoting arm, and a second opening is in a proximal portion of the second pivoting arm. A first concave segment is coupled to at least one of a first pivoting arm and a second pivoting arm. Also included is a first facet rod. The method further comprises positioning the first pivoting arm on a surface of a superior vertebral facet of a first vertebra by pivoting the first pivoting arm about the hinge. The method further comprises positioning the second pivoting arm on a surface of an inferior vertebral facet of a second vertebra by pivoting the second pivoting arm about the hinge. The method further comprises placing the facet rod through the opening in the proximal portion of the first pivoting arm, the superior vertebral facet of the first vertebra, the inferior vertebral facet of the second vertebra, and the opening in the proximal portion of the second pivoting arm, fixing the surgical device to the vertebral facet joint.

In an embodiment, at least one of the opening in the proximal portion of the first pivoting arm and the opening in the proximal portion of the second pivoting arm comprises an oblong shape. In an embodiment, positioning comprises moving at least one of the first pivoting arm and the second pivoting arm back and forth on the surface of a vertebral facet so that a position of the first device is modified relative to a position of the rod. In an embodiment, the first pivoting arm and the second pivoting arm pivot independently. In an embodiment, the first pivoting arm and the second pivoting arm pivot together to the same degree automatically when one of the first pivoting arm and the second pivoting arm is pivoted.

Also provided herein is a method for fixing vertebrae. The method comprises receiving a first surgical device comprising a first hinge, a first pivoting arm extending from the first hinge, and a second pivoting arm extending from the first hinge. A first opening is in a proximal portion of the first pivoting arm and a second opening is in a proximal portion of the second pivoting arm; a first concave segment coupled to at least one of the first pivoting arm and the second pivoting arm. Also included is a first facet rod. The method further comprises receiving a second surgical device comprising a second hinge, a third pivoting arm extending from the second hinge, a fourth pivoting arm extending from the second hinge. There is included an opening in a proximal portion of the third pivoting arm, and an opening in a proximal portion of the fourth pivoting arm as well as a second concave segment coupled to at least one of the third pivoting arm and the fourth pivoting arm. Also included is a second facet rod. The method further comprises positioning the first pivoting arm on a surface of a superior vertebral facet of a first vertebra by pivoting the first pivoting arm about the first hinge; positioning the second pivoting arm on a surface of an inferior vertebral facet of a second vertebra by pivoting the second pivoting arm about the first hinge. The method further comprises positioning the third pivoting arm on a surface of a superior vertebral facet of a third vertebra by pivoting the third pivoting arm about the second hinge. The method further comprises positioning the fourth pivoting arm on a surface of an inferior vertebral facet of the first vertebra by pivoting the fourth pivoting arm about the second hinge. The method further comprises placing the first rod through the opening in the proximal portion of the first pivoting arm, the superior vertebral facet of the first vertebra, the inferior vertebral facet of the second vertebra, and the opening in the proximal portion of the second pivoting arm; placing the second rod through the opening in the proximal portion of the third pivoting arm, the superior vertebral facet of the third vertebra, the inferior vertebral facet of the first vertebra, and the opening in the proximal portion of the second pivoting arm. The method further comprises coupling a multi-level rod to the first concave segment, and coupling the multi-level rod to the second concave segment, thereby fixing the first vertebra, the second vertebra, and the third vertebra.

In an embodiment, at least one of the opening in the proximal portion of the first pivoting arm and the opening in the proximal portion of the second pivoting arm, and at least one of the opening in the third pivoting arm and the opening in the fourth pivoting arm comprises an oblong shape. In an embodiment, positioning comprises moving at least one of the first pivoting arm, the second pivoting arm, the third pivoting arm, and the fourth pivoting arm back and forth on the surface of a vertebral facet so that a position of at least one of the first device and the second device is modified relative to a position of at least one of the first rod and the second rod. In an embodiment, the first pivoting arm and the second pivoting arm pivot independently. In an embodiment, the third pivoting arm and the forth pivoting arm pivot independently. In an embodiment, the first pivoting arm and the second pivoting arm pivot together to the same degree automatically when one of the first pivoting arm and the second pivoting arm is pivoted. In an embodiment, the third pivoting arm and the fourth pivoting arm pivot together to the same degree automatically when one of the third pivoting arm and the fourth pivoting arm is pivoted. In an embodiment, the first hinge couples with the first pivoting arm and the second pivoting arm. In an embodiment, the second hinge couples with the third pivoting arm and the fourth pivoting arm.

Also described herein is a vertebral fixation device comprising a body having a superior, an inferior, a lateral, and a posterior wall. The superior, inferior, and posterior walls join to form a recess within the body that is configured to receive a vertebral facet joint within the recess. A lateral wall may be positioned over a lateral side of the body and may be configured to enclose the recess within the body on only a single lateral side of the body. The body may further comprise a first opening through the superior wall of the body and a second opening through the inferior wall of the body, wherein the second opening is positioned on the inferior wall of the body to receive a screw passed through the first opening at a first angle.

In an embodiment, the posterior wall of the body is coupled to a coupler configured to couple to a reticulating coupler configured to couple to a rod. In an embodiment, the coupler comprises a spherical shape. In an embodiment, the reticulating coupler comprises a tulip.

In an embodiment, the vertebral fixation device further comprises a third opening through the inferior wall of the body, wherein the third opening is positioned on the inferior wall of the body to receive a screw passed through the first opening at a second angle.

In an embodiment, the body further comprises a coupler on the superior wall configured to couple with a drill guide. In an embodiment, the coupler comprises an indentation in the superior wall of the body configured to receive a protrusion on the drill guide.

Also described herein is a vertebral fixation system, comprising a first body comprising a first superior, a first inferior, a first lateral, and a first posterior wall. The first superior, first inferior, and first posterior walls may join to form a recess within the first body that is configured to receive a first vertebral facet joint within the recess of the first body, and wherein the first lateral wall is positioned over a right lateral side of the first body and is configured to enclose the recess within the first body on only a single lateral side of the first body. A vertebral fixation system may further comprise a first opening through the first superior wall of the first body and a second opening through the first inferior wall of the first body, wherein the second opening is positioned on the first inferior wall of the first body to receive a first screw passed through the first opening at a first angle. A vertebral fixation system further comprises a second body comprising a second superior, a second inferior, a second lateral, and a second posterior wall. The second superior, second inferior, and second posterior walls may join to form a recess within the second body that is configured to receive a second vertebral facet joint within the recess of the second body, and wherein the second lateral wall is positioned over a right lateral side of the second body and is configured to enclose the recess within the second body on only a single lateral side of the second body. A vertebral fixation system may further comprise a third opening through the first superior wall of the first body and a fourth opening through the first inferior wall of the first body, wherein the fourth opening is positioned on the first inferior wall of the first body to receive a second screw passed through the third opening at a second angle. A vertebral fixation system may further comprise a rod configured to couple to the first and the second bodies.

In an embodiment, the first or the second posterior wall of the first or the second body is coupled to a first or second coupler configured to couple to a first or second reticulating coupler configured to couple to the rod. In an embodiment, the coupler comprises a spherical shape. In an embodiment, the reticulating coupler comprises a tulip.

In an embodiment, a vertebral fixation system further comprising a coupler on the first and the second superior wall configured to couple with a drill guide. In an embodiment, the coupler comprises an indentation in the first and second superior wall of the first and second bodies configured to receive a protrusion on the drill guide.

Also described herein is a method for vertebral fixation. The method comprises the step of engaging a first vertebral facet joint within a recess of a first vertebral fixation device, wherein the first vertebral fixation device is configured to receive a first vertebral facet joint within the recess, and further comprises a first and a second opening and a first articulating coupler. The method comprises the step of engaging a second vertebral facet joint within a recess of a second vertebral fixation device, wherein the second vertebral fixation device is configured to receive a second vertebral facet joint within the recess, and further comprises a third and a fourth opening and a second articulating coupler. The method comprises the step of passing a screw through the first opening in the first vertebral fixation device, through the first vertebral facet joint, and through the second opening in the first vertebral fixation device while the first vertebral fixation device is engaged with the first vertebral facet joint. The method comprises the step of passing a screw through the third opening in the first vertebral fixation device, through the second vertebral facet joint, and through the fourth opening in the second vertebral fixation device while the second vertebral fixation device is engaged with the second vertebral facet joint. The method comprises the step of coupling the first and the second vertebral fixation devices with a rod coupled to the first and second articulating couplers.

Also described herein is a vertebral fixation method. The vertebral fixation method comprises coupling a first vertebral fixation device with a first superior facet of a first facet joint, wherein the first vertebral fixation device comprises a recess enclosed by a first superior wall, a first posterior wall, a first inferior wall, and a first lateral wall, wherein at least a portion of the first superior facet is positioned within the recess, and wherein the first inferior wall is positioned between the first superior facet and a first inferior facet of the first facet joint.

In an embodiment, the method further comprises coupling a second vertebral fixation device with a second superior facet of a second facet joint, wherein the second vertebral fixation device comprises a recess enclosed by a first superior wall, a second posterior wall, a second inferior wall, and a second lateral wall, wherein at least a portion of the second superior facet is positioned within the recess, and wherein the second inferior wall is positioned between the second superior facet and a second inferior facet of the second facet joint, and fixing a horizontal rod to the first and second vertebral fixation devices. In an embodiment, the horizontal rod is fixed to the first and second vertebral fixation devices so that a compressive force is applied to a first and second vertebral facet joint by the first and second vertebral fixation devices. In an embodiment, the first lateral wall is a right lateral wall, the second lateral wall is a left lateral wall, the first facet joint is a right facet joint, and the second facet joint is a left facet joint. In an embodiment, the horizontal rod fixes to the first and second vertebral fixation devices by coupling with a first articulating coupler of the first vertebral fixation device and a second articulating coupler of a second vertebral fixation device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the surgical device described herein are set forth with particularity in the appended claims. A better understanding of the features and advantages of the present invention will be obtained by reference to the following detailed description that sets forth illustrative embodiments, in which the principles of the surgical device described herein are utilized, and the accompanying drawings of which:

DETAILED DESCRIPTION

Figure 1:
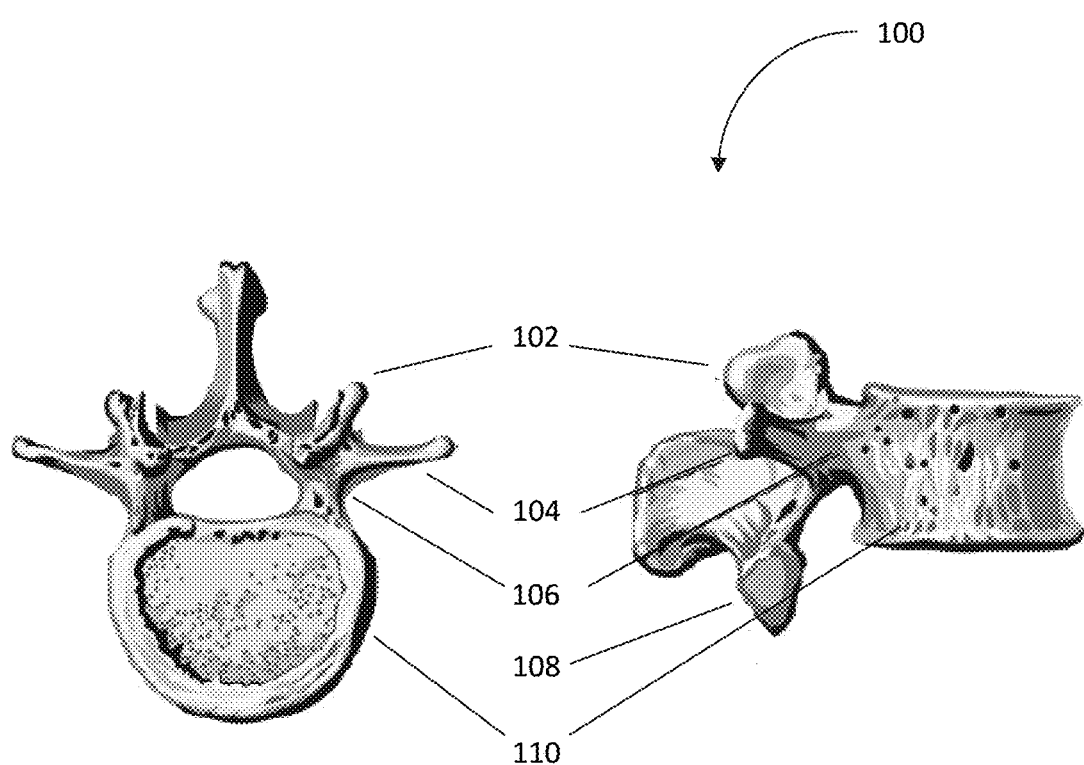
FIG. 1 shows a superior and lateral view of a lumbar vertebra.

Before describing the subject matter disclosed herein in detail, it is to be understood that the subject matter is not limited in its application to the details of construction, experiments, exemplary data, and/or the arrangement of the components set forth in the following description, or illustrated in the drawings. The subject matter described herein is capable of other embodiments, and therefore the embodiments described herein should not be taken to limit the scope of the subject matter of the description in any way. Also, it is to be understood that the phraseology and terminology employed herein is for the purpose of description only and should not be regarded as limiting in any way.

The term "proximal" may be used to describe positions, locations, or orientations of the orthopedic devices and methods described herein or components of the orthopedic devices. Unless specified otherwise, the term "proximal" refers to a position, location, or orientation with reference to engagement or coupling of the device with a vertebral facet joint. That is, for example, a proximal portion of the device is a portion of the device that will be in proximity to a vertebral facet joint when the device may engage or couple with the vertebral facet joint.

The term "distal" may be used to describe positions, locations, or orientations of the orthopedic devices and methods described herein or components of the orthopedic devices. Unless specified otherwise, the term "proximal" refers to a position, location, or orientation with reference to engagement or coupling of the device with a vertebral facet joint. That is, for example, a distal portion of the device is a portion of the device that will not be in proximity to a vertebral facet joint when the device may engage or couple with the vertebral facet joint.

The terms "in" and "through" may be used interchangeably in describing the position of an opening in relation to a wall or a surface.

Described herein are devices, systems, and methods for use in vertebral fixation procedures. More specifically, described herein are devices, systems, and methods for achieving spinal fixation comprising fixing together adjacent facets at a facet joint.

Described herein are devices, systems, and methods for use between two facets that form a facet joint. That is, described herein are devices that are positioned between a superior and inferior facet of the same facet joint. For example, in an embodiment of a vertebral fixation device, at least one portion of a vertebral fixation device is positioned between a superior and inferior facet of a facet joint when the vertebral fixation device is coupled with a vertebral facet joint. In an embodiment, a vertebral fixation device is configured to receive or couple with either or both a superior and inferior facet.

Described herein are devices, systems, and methods for coupling to the vertebral facet joint. In an embodiment, a vertebral fixation device is configured to couple with the vertebral facet joint and is not positioned between a superior and inferior facet.

Described herein are devices, systems, and methods for providing horizontal compression to the spine at the vertebral facet joints. For example, in an embodiment, a right vertebral fixation device comprises a right lateral wall or shield and a left vertebral fixation device comprises a left lateral shield. In an embodiment, when the right vertebral fixation device is coupled to a right facet joint and the left vertebral facet is coupled to a left vertebral facet joint the right and left lateral shields are positioned respectively on the right lateral side of a vertebral facet joint and the left lateral side of a vertebral facet joint. In an embodiment, when the right and left lateral shields are brought together under tension, by for example, a horizontal connecting rod, the right lateral shield applies compression to the right vertebral facet joint and left shield applies compression to the left vertebral facet joint.

Described herein are devices, systems, and methods for use between two facets that form a facet joint that are also configured to provide horizontal compression to the spine at the vertebral facet joints.

FIG. 1 shows a superior and lateral view of a lumbar vertebra 100. Vertebrae are positioned in a column, and two adjacent vertebrae will articulate at a vertebral facet joint. A facet joint comprises a superior facet 102 coupled with an inferior facet 108. The superior facet 102 and inferior facet 108 are each a part of different adjacent vertebrae within the spinal column.

That is, a superior facet 102 of a first vertebra will articulate with an inferior facet 108 of a second vertebra positioned above (or cranial to) and adjacent to the first vertebra within the vertebral column. For example a superior facet of lumbar vertebra L4 will form a vertebral facet joint together with an inferior facet of lumbar vertebra L3.

A vertebral facet joint is a type of facet joint formed between two vertebrae. For example, there are typically two facet joints between lumbar vertebra L3 and L4. A facet joint is positioned on each side of the vertebral midline.

A vertebra further comprises a transverse process 104, a pedicle 106, and a vertebral body 110. The vertebral body 110 of a first vertebra is separated from the vertebral body 110 of a second vertebra that is adjacent to it by an intervertebral disc.

Spinal nerves (not shown) travel out and away from the spinal column through foramen formed superiorly and inferiorly by the pedicles 106 of two adjacent vertebrae. Spinal nerves typically travel anterior to the vertebral transverse process 104.

Figure 2:
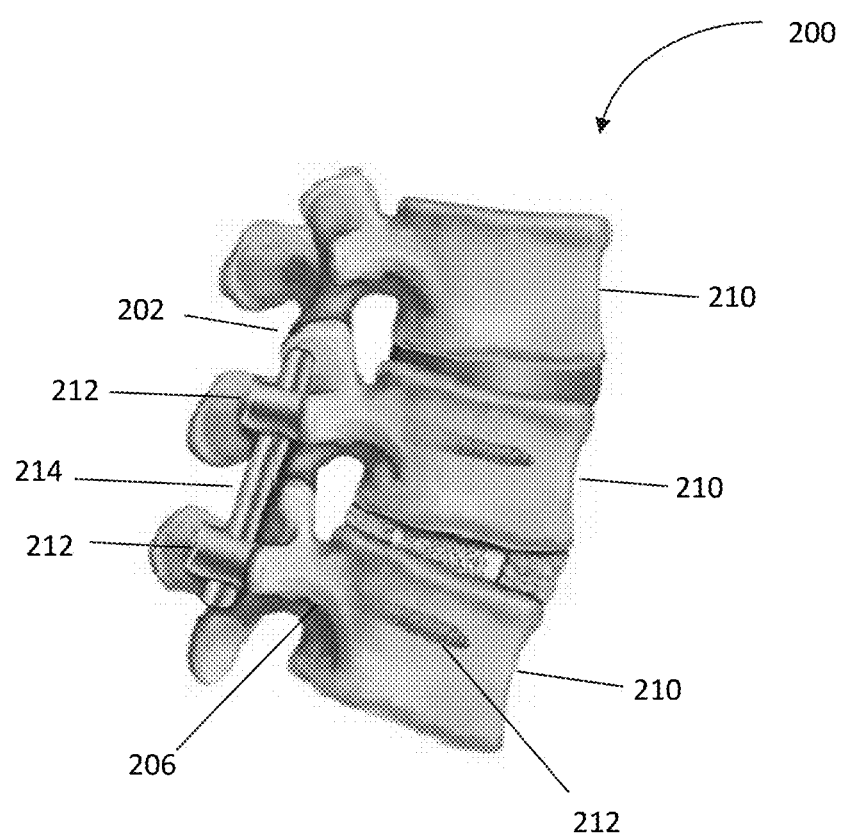
FIG. 2 shows a lateral view of the result of a typical traditional spinal fusion procedure.

FIG. 2 shows a lateral view of the result of a typical traditional spinal fusion procedure 200. Two large pedicle screws 212 are placed through the pedicles 206 of adjacent vertebra. Each pedicle screw 212 is drilled into the vertebral body 210 (translucent), fixing the pedicle screw 212 into a fixed position.

Rod 214 attaches to two or more fixed adjacent pedicle screws 212.

Because the pedicle screw 212 is fixed to the vertebra by virtue of being embedded in the pedicle 206 and vertebral body 210, fixing the pedicle screws 212 together with the multi-level rod 214, also fixes together the vertebrae in which the pedicle screws 212 are embedded. For example, the two vertebrae in FIG. 2, through which pedicle screws 212 are embedded, are fixed.

It should be noted that while not shown, two more pedicle screws 212 and an additional multi-level rod 214 are present on the other side of the image of the traditional fixation. The other two pedicle screws 212 are embedded through pedicles corresponding to the same two fixed vertebrae, and those two pedicles are connected by a multi-level rod 214 as well. That is, fixation of two vertebrae in the fashion shown, typically requires four pedicle screws 212 and two multi-level rods 214.

Multi-level rod 214 acts as a scaffold holding two or more adjacent pedicles screws 212 in a fixed position relative to each other. In this way, by fixing the distance and position of the pedicle screws 212 relative to each other, the multi-level rod 214 can also fix the positions of the vertebrae in which the pedicle screws 212 are embedded.

Fixing vertebrae in place with a spinal fusion procedure can treat, for example, a collapse of one vertebra onto another due to intervertebral disc disease. The mechanical fusion of the vertebra that the procedure creates can prevent an abnormally moving vertebra or multiple abnormally moving vertebrae from compressing a spinal nerve due to, for example, the vertebra or vertebrae moving into a non-anatomical position. Compression of spinal nerves can cause severe radiating pain along the distribution of the compressed nerve, and removal of the compression typically resolves or at least ameliorates the pain.

Traditional spinal fusion is highly invasive, because it requires that large and bulky pedicle screws 212 be placed deep into the vertebral bodies 210 of the vertebrae. The large and bulky pedicle screws 212 are also placed dangerously close to spinal nerves, when pedicle screws 212 pass through the vertebral pedicles 206, which are immediately above and below spinal nerves.

The positioning of the pedicle screws 212 is the most essential and complex part of the traditional spinal fusion procedure, as a misplaced pedicle screw 212 can injure or compress a nerve. Pedicle screws 212 are typically positioned and placed based on the estimation of the surgeon rather than more objective criteria, which can contribute errors. A complication of traditional spinal fusion is a misplaced pedicle screw 212 that injures, pinches, or compresses a spinal nerve near the location of a pedicle screw 212's insertion into a pedicle 206. The particular complication, of an injured, pinched, or compressed nerve due to a misplaced pedicle screw 212, typically requires reoperation. Upon reoperation, adjustment of the misplaced pedicle screw 212 is often not possible, because a large opening was already been placed in the pedicle 206 when the pedicle screw 212 was originally fixed in place improperly.

The orthopedic surgical device described herein is far less bulky and invasive than the traditional pedicle screw 212, and will dramatically lower or completely eliminate the risk of injury, pinching, or compression of a spinal nerve, because the device is fixed to a different area of the vertebra.

Rather than being fixed through the pedicle 206 and vertebral body 210, the presently described device is fixed through the vertebral facet joint of the vertebrae, which as shown in FIG. 1, comprises of the superior and inferior facets 102 and 108 of two adjacent vertebrae. By piercing through the facet joint, the presently described device fixes two adjacent vertebrae to each other at the facet joint rather than at the pedicle 206 as would be done with the traditional spinal fixation procedure.

The facet joint, unlike the pedicle 206, is located posterior to and away from the exiting spinal nerve. Plus, the facet joint is essentially shielded from the spinal nerve by the transverse process 104. Thus, compression of a nerve due to the presently described device would be highly unlikely. Because the presently described device need only be affixed to an area of the vertebrae that is small in size, the device itself is small in size relative to a traditional pedicle screw 212. Similarly because the device need only penetrate the facet rather than the much larger vertebral body 210, the device need not be bulky.

Figure 3:
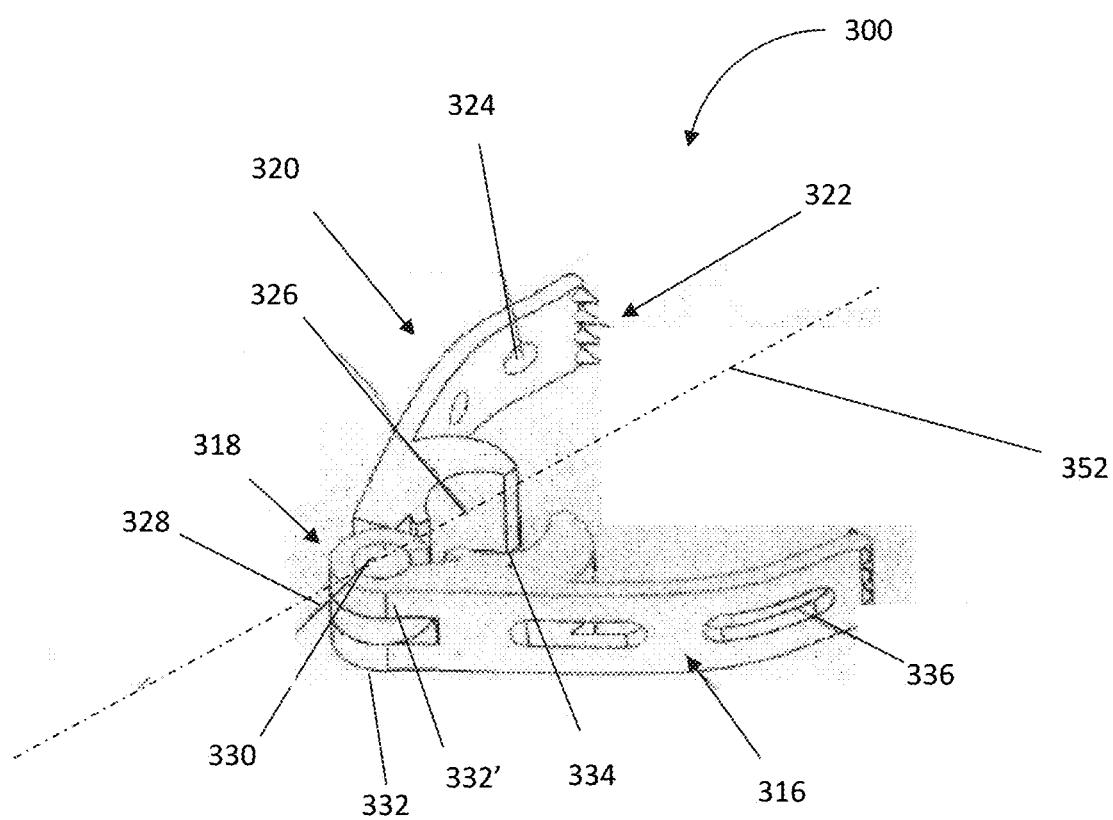
FIG. 3 shows an embodiment of the described orthopedic device.

FIG. 3 shows an embodiment of an orthopedic device 300 as described herein. The device 300 is essentially shaped like a clip with a hinge 318 at one end that allows a first pivoting arm 316 and a second pivoting arm 320 to open and close or to pivot about the hinge 318.

The device 300 has a proximal end that is configured to engage with a vertebra and a distal end on which a hinge 318 is positioned. Similarly, each arm of the device 300 has a proximal end that is configured to engage with a vertebra and a distal end that may form a hinge 318 or be coupled to a hinge 318. The hinge 318 both allows the first pivoting arm 316 and the second pivoting arm 320 to pivot and to fasten to the vertebral facet joint.

In an embodiment, the distal end of a first pivoting arm 316 may comprise of two loops 332, 332' positioned in a column with one loop directly above the other. The two loops 332, 332' are spaced apart so that there is a space in between them. The distal portion of the second pivoting arm 320 may comprise of a single loop 328 that is positioned so that it will fit in between the two loops 332, 332' of the first pivoting arm 316. The loop at the proximal end of the second pivoting arm 320 is also positioned so that when the loop of the second pivoting arm 320 fits in between the two loops 332, 332' of the first pivoting arm 316, the first pivoting arm 316 and the second pivoting arm 320 are aligned within the same horizontal axis or level.

The two loops 332, 332' of the first pivoting arm 316 and the single loop 328 of the second pivoting arm 320 may be fitted together in a contiguous or nearly contiguous column, comprising from top to bottom of the first of two loops 332' on the distal end of the first pivoting arm 316, the single loop 328 of the distal end of the second pivoting arm 320, and the second of two loops 332 on the distal end of the first pivoting arm 316. The column is formed such that the openings within the three loops are lined up together forming a continuous passage through the column of three loops. A short hinge rod 330 may be placed or fixed within the continuous openings of the column fixing them together in this formation and creating an axis around which each arm is able to individually pivot.

As the first pivoting arm 316 and the second pivoting arm 320 open and close or pivot about the hinge rod 330 of the hinge 318, the first pivoting arm 316 and the second pivoting arm 320 remain in the same horizontal plane. This is similar to a traditional hinge as found, for example, on a door.

Similar embodiments on the hinge 318 are also possible and known to those having skill in the art. Other non-limiting embodiments of suitable hinges may include a hinge with two interlocking loops or a hinge with four or more interlocking loops. The means of forming a column need not be through loops, but can also be done through the use of hooks, triangles, squares, or other polygonal shapes, and various clips. The hinge rod 330 may be a cylindrical shape or any other suitable shapes that will fix together the components of the column, for example, loops, and provide an axis around which the arms of the device 300 are able to pivot. Non-limiting suitable examples of rods may include multiple cylindrical rods, elliptical rods or other circular shapes, and various polygonal shapes.

Alternatively, the components of the column that form the hinge 318, for example, loops, may be fixed together by other means that do not include a hinge rod 330 passing through their openings. Non-limiting examples of ways to fix the components of the column that form the hinge 318 include tying the elements together, having them snap fit with each other, or having them threadably interlock.

In an embodiment, a hinge 318 may be a separate component that is attached to both the first 316 and second 320 pivoting arms of the device 300. For example, a hinge 318 comprising of a column of loops with a hinge rod 330 there through, may be attached to both the first 316 and second 320 pivoting arms via, for example, two plates that are attached respectively to each arm. This is similar to the hinges on a door frame. Other non-limiting examples for attaching a hinge 318 to a distal portion of a first pivoting arm 316 and a second pivoting arm 320 includes fusing the hinge 318 to the distal portion of a first pivoting arm 316 and a second pivoting arm 320 through welding or gluing.

When the device 300 is deployed, at least a portion of the first pivoting arm 316 and the second pivoting arm 320 of the device 300 close or clamp around the outside surface of the vertebral facet joint.

Because the vertebral facet joint is a relatively small part of the intervertebral structure, the device 300 itself is relatively small, and the device 300 is typically significantly smaller than a typical pedicle screw 212.

The device 300 may, for example, measure about 1 cm in total length. Alternatively, the device 300 may, for example, measure about 1.25 cm in total length. Alternatively, the device 300 may, for example, measure about 1.5 cm in total length. Alternatively, the device 300 may, for example, measure about 1.75 cm in total length. Alternatively, the device 300 may, for example, measure about 2 cm in total length. Alternatively, the device 300 may, for example, measure about 2.25 cm in total length. Alternatively, the device 300 may, for example, measure about 2.5 cm in total length. Alternatively, the device 300 may, for example, measure about 2.75 cm in total length. Alternatively, the device 300 may, for example, measure about 3 cm in total length. Alternatively, the device 300 may, for example, measure about 3.25 cm in total length. Alternatively, the device 300 may, for example, measure about 3.5 cm in total length. Alternatively, the device 300 may, for example, measure about 3.75 cm in total length. Alternatively, the device 300 may, for example, measure about 4 cm in total length. Alternatively, the device 300 may, for example, measure about 4.25 cm in total length. Alternatively, the device 300 may, for example, measure about 4.5 cm in total length. Alternatively, the device 300 may, for example, measure about 4.75 cm in total length. Alternatively, the device 300 may, for example, measure about 5 cm in total length. Various different lengths may, for example, be suitable for use in different patients, as vertebral anatomy and vertebral size vary from patient to patient. Alternatively, longer devices may be used in combination with shorter devices in the same patient to, for example, adjust for a curvature in patient's spine that affects the alignment of the vertebrae in the vertebral column.

In an embodiment, the first pivoting arm 316 and the second pivoting arm 320 are rectangular.

In an embodiment, the first pivoting arm 316 and the second pivoting arm 320 comprise concave shapes that curve towards the interior midline 352 of the device 300 within the horizontal plane of the device 300. That is each of the first pivoting arm 316 and the second pivoting arm 320 form concave arcs towards the midline 352 of the device 300.

In an embodiment, the arc of the curved first pivoting arm 316 and the second pivoting arm 320 may be located towards the proximal ends of the first pivoting arm 316 and the second pivoting arm 320 rather than, for example, in the middle of the length of the pivoting arms.

In an embodiment, the arc of the curved the first pivoting arm 316 and the second pivoting arm 320 may be located towards the middle of the lengths the first pivoting arm 316 and the second pivoting arm 320.

In an embodiment, the arc of the curved the first pivoting arm 316 and the second pivoting arm 320 may be located towards the distal ends of the pivoting arms.

The length of the first pivoting arm 316 and the second pivoting arm 320 may, for example, be equal to the length of the device 300.

In embodiment, the length of the first pivoting arm 316 and the second pivoting arm 320, may be, for example, less than the length of the device 300.

The height of the device 300 may be around 0.25 cm. Alternatively, the height of the device 300 may be around 0.5 cm. Alternatively, the height of the device 300 may be around 0.75 cm. Alternatively, the height of the device 300 may be around 1 cm. Alternatively, the height of the device 300 may be around 1.25 cm. Alternatively, the height of the device 300 may be around 1.50 cm.

The width of the first pivoting arm 316 and the second pivoting arm 320 may be consistent throughout the device 300 or alternatively the width may taper in a proximal or distal direction along the length of the first pivoting arm 316 and the second pivoting arm 320. The shortest width of the first pivoting arm 316 and the second pivoting arm 320 may be around 1 mm. Alternatively, the shortest width of the first pivoting arm 316 and the second pivoting arm 320 may be around 1.25 mm. Alternatively, the shortest width of the first pivoting arm 316 and the second pivoting arm 320 may be around 1.5 mm. Alternatively, the shortest width of the first pivoting arm 316 and the second pivoting arm 320 may be around 1.75 mm. Alternatively, the shortest width of the first pivoting arm 316 and the second pivoting arm 320 may be around 2 mm. Alternatively, the shortest width of the first pivoting arm 316 and the second pivoting arm 320 may be around 2.25 mm. Alternatively, the shortest width of the first pivoting arm 316 and the second pivoting arm 320 may be around 2.5 mm. Alternatively, the shortest width of the first pivoting arm 316 and the second pivoting arm 320 may be around 2.75 mm. Alternatively, the shortest width of the first pivoting arm 316 and the second pivoting arm 320 may be around 3.0 mm. Alternatively, the shortest width of the first pivoting arm 316 and the second pivoting arm 320 may be around 3.25 mm. Alternatively, the shortest width of the first pivoting arm 316 and the second pivoting arm 320 may be around 3.5 mm.

The first pivoting arm 316 and the second pivoting arm 320 may be made to pivot over different ranges of degrees. The range of pivoting of the first pivoting arm 316 and the second pivoting arm 320 may be made to extend from zero degrees to 180 degrees relative to the horizontal midline of the device 300. Alternatively, the range of pivoting of the first pivoting arm 316 and the second pivoting arm 320 may be made to extend from zero degrees to 135 degrees relative to the horizontal midline of the device 300. Alternatively the range of pivoting of the first pivoting arm 316 and the second pivoting arm 320 may be made to extend from zero degrees to 90 degrees relative to the horizontal midline of the device 300.

The first pivoting arm 316 and the second pivoting arm 320 may, for example, pivot independently of the other arm. That is, a first pivoting arm 316 may, for example, be pivoted by a user to 30 degrees relative to the horizontal midline of the device 300, while the second pivoting arm 320 does not change position relative to the horizontal midline of the device 300. In this way, the pivoting arms of the device 300 may be pivoted to different degrees from the horizontal midline of the device 300, and the pivoting of one arm does not affect or modify the position of the other arm.

Alternatively, in an embodiment, the hinge 318 column components, which may be, for example, loops, are all attached to the hinge rod 330 inside the hinge 318 at a single point along the length of the hinge rod 330. When one of the first pivoting arm 316 and the second pivoting arm 320 is pivoted, the hinge rod 330 turns with it, because they are attached. The turning of the hinge rod 330 in for example a clockwise direction, will simultaneously cause the pivoting arm on the opposite side to pivot to an equal degree as the first pivoting arm that was pivoted. Thus, in this embodiment, the first pivoting arm 316 and the second pivoting arm 320 may pivot together to an equal degree. That is, if one of the pivoting arms is pivoted to 30 degrees from the central axis, the other pivoting arm will automatically be pivoted to the same degree on the opposite side. This embodiment may be advantageous for efficient repositioning of the device 300 within a space that is difficult to enter with a finger or an instrument. This mechanical means for generating reciprocal movement in the first pivoting arm 316 and the second pivoting arm 320 is meant as a non-limiting example only, as there are other means for achieving the same goal. A non-limiting example of a mechanical means for achieving reciprocal movement in the first pivoting arm 316 and the second pivoting arm 320 is with, for example, use of a ball bearing mechanism similar to that found in, for example, a compass.

The device 300 comprises of a retaining element 322 positioned at the proximal end of the device 300, wherein the retaining elements 322 assists in securing or fixing the device 300 to the surface of a vertebral facet.

The retaining element 322 may transiently or reversibly secure the device 300 to a vertebral facet when the arms of the device 300 are closed around the facet, but the device 300 has not yet been fixed to the surface of the superior and inferior vertebral facets. Transiently or reversibly securing the device 300 to the facet provides the surgeon with, for example, the ability to position multiple devices on multiple vertebrae relative to each other before fixing the device 300 or multiple devices in position. Or, for example, the ability to transiently or reversibly secure the device 300 to a vertebral facet may provide the surgeon with the ability to carefully set the angle of fixation of the device 300 before permanently fixing the device 300 to the facet. The ability to determine the ideal angle of the device 300 is important in order to optimally attach a multi-level rod to multiple devices on different vertebrae. The ideal angle of each device 300 relative to the multi-level rod will likely be different for each facet and each patient. The ideal positioning of the device 300 will allow for attachment of the multi-level rod in a manner that does not place any unintended tension on the vertebrae or surrounding tissues or cause compression. The retaining element 322 may alternatively and/or additionally facilitate the fixation of the device 300 to the vertebral facet joint.

Generally, the device 300 is fixed to the vertebral facet joint by tightly fixing the pivoting arms against the surfaces of the respective vertebral facets. The retaining element 322 may facilitate or tighten the connection of the first pivoting arm 316 and the second pivoting arm 320 to the respective surface of the vertebral facets by forming an additional attachment to the surface of a vertebral facet. That is, for example, the retaining element 322 may penetrate into the surface of the vertebral facet thereby grabbing on or biting into the surface of the facet.

The retaining element 322 is positioned at the proximal end of the device 300 and, thereby, at the proximal ends of each of the first pivoting arm 316 and the second pivoting arm 320.

The retaining element 322 may comprise protrusions that may, for example, penetrate the boney surface of a vertebral facet. The protrusions may be sharp or smooth. In one embodiment, the protrusions are sharp teeth. In one embodiment, the protrusions are smooth surfaced bullet shaped cylinders.

Alternatively, rather than protrusions, the retaining element 322 may comprise a rough or texturized surface. Non-limiting examples of such surfaces include surfaces that are knurled or splined. Such surfaces may, for example, increase grip without fully penetrating the vertebral facet's surface.

The first pivoting arm 316 and the second pivoting arm 320 of the device 300 each also comprise at least one opening 324 or opening 336 preferably in their proximal aspect. The at least one opening 324 or opening 336 may be positioned on each the first pivoting arm 316 and the second pivoting arm 320 of the device 300 so that the opening 324 or opening 336 on the first pivoting arm 316 and the second pivoting arm 320 is positioned essentially directly across from the opening 324 or opening 336 in the other arm.

When the device 300 is fixed into the vertebral facet, a bar or rod is passed through an opening in the first pivoting arm, through an opening in the facet, and through the opening in the second pivoting arm. In an embodiment, an opening 336 in each of the first pivoting arm 316 and the second pivoting arm 320 is oblong and extends for a length along the proximal aspect of the first pivoting arm 316 and the second pivoting arm 320.

The oblong opening 336 allows, for example, for the position of the first pivoting arm 316 and the second pivoting arm 320 to be adjusted relative to the position of a facet rod that passes through the opening 324 or opening 336 on each of the first pivoting arm 316 and the second pivoting arm 320. This embodiment can be advantageous in a scenario wherein, for example, the facet rod does not traverse the facet in an ideal way such as, for example, the facet rod does not exit the facet where it was expected to exit. In this scenario with the oblong opening embodiment, one or both the first pivoting arm 316 and the second pivoting arm 320 may be slidably adjusted along the facet rod, thereby, correcting or adjusting the position of the device 300.

A facet rod may fix the device 300 to the facet joint through a number of different ways. In a first embodiment, a facet rod and openings 324 on the device 300 may be threaded so that the device 300 and facet rod threadably engage with each other tightening the first pivoting arm 316 and the second pivoting arm 320 of the device 300 against the surface of the facet when they threadably engage. In an embodiment, the facet rod may be a bolt with a nut that threadably engages with its distal end pressing the first pivoting arm 316 and the second pivoting arm 320 of the device 300 against the surface of the vertebral facet joint. Washers may be used in addition to either the threaded facet rod or bolted facet rod embodiment, in order to more tightly press the first pivoting arm 316 and the second pivoting arm 320 of the device 300 against the surface of the vertebral facet joint.

The device 300 is configured to attach to a multi-level rod. A multi-level rod is a rod that may attach to multiple devices on multiple facets joints on the same side of the vertebral column. The multi-level rod is typically positioned essentially vertically relative to the vertebral column. Because a fixation typically requires placing devices on both sides of the vertebral column, there are typically two multi-level rods used in a multi-level fixation. For example, a fixation of lumbar vertebra L2, L3, L4, and L5 would typically involve six devices and two multi-level rods. That is, two devices on each of six facet joints and two multi-level rods. Each one of the multi-level rods would attach to and fix three devices together, thus fixing the vertebra to which the devices are attached.

The device 300 comprises a component for engaging with a multi-level rod. In an embodiment, the device 300 comprises two concave segments 326 and 334 along the posterior portion of the first pivoting arm 316 and the second pivoting arm 320. The concave segments are sized to tightly wrap around the multi-level rod when the proximal portion of the first pivoting arm 316 and the second pivoting arm 320 are closed around or clamped onto the respective surface of the vertebral facets. That is, when the first pivoting arm 316 and the second pivoting arm 320 are brought together the concave segments 326 and 334 may come together around a multi-level rod. When for example, the proximal portions of the first pivoting arm 316 and the second pivoting arm 320 are tightly held against the surface of the vertebral facet, the concave segments 326 and 334 are similarly tightly held against the multi-level rod, fixing the device 300 to the multi-level rod.

In an embodiment the device comprises of only one groove segment coupled to a pivoting arm, and the multi-level rod is secured by the single groove segment coupled to a first pivoting arm and the second pivoting arm.

In an embodiment, the surface of at least one of the concave segments 326 and 334 are serrated or rough to facilitate a tight connection around the multi-level rod.

Suitable material for forming the device 300 includes durable metals such as, for example, titanium or steal.

Figure 4:
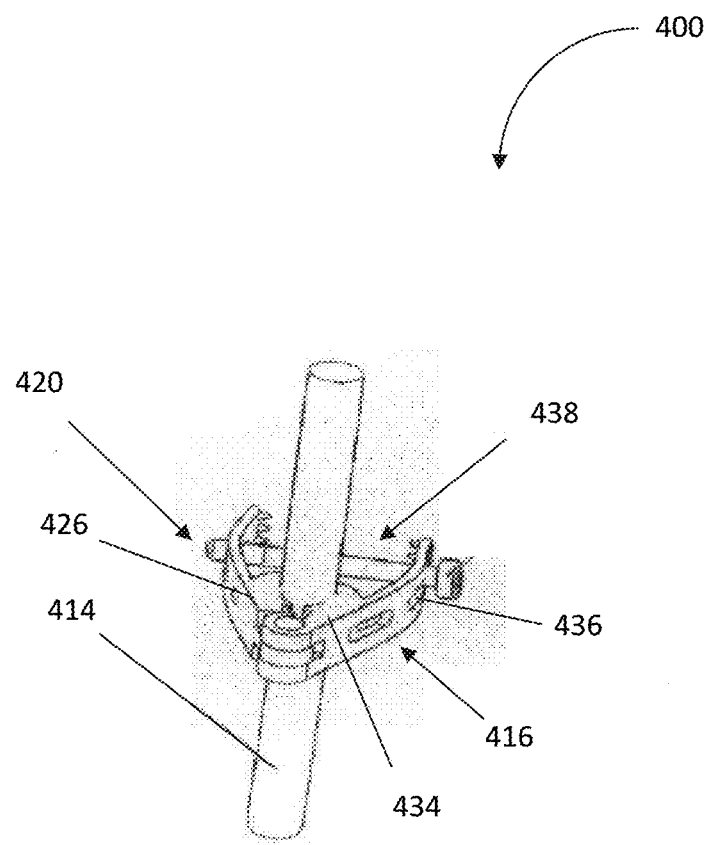
FIG. 4 shows how the concave segments tightly surround a multi-level rod from a posterior view of the device.

FIG. 4 shows how the concave segments 426, 434 of the device 400 tightly surround a multi-level rod 414 from a posterior view of the device 400. Also, shown, is a facet rod 438 with the bolt embodiment for tightly fixing the first pivoting arm 416 and the second pivoting arm 420 to the respective surface of the vertebral facet (not shown).

Figure 5:
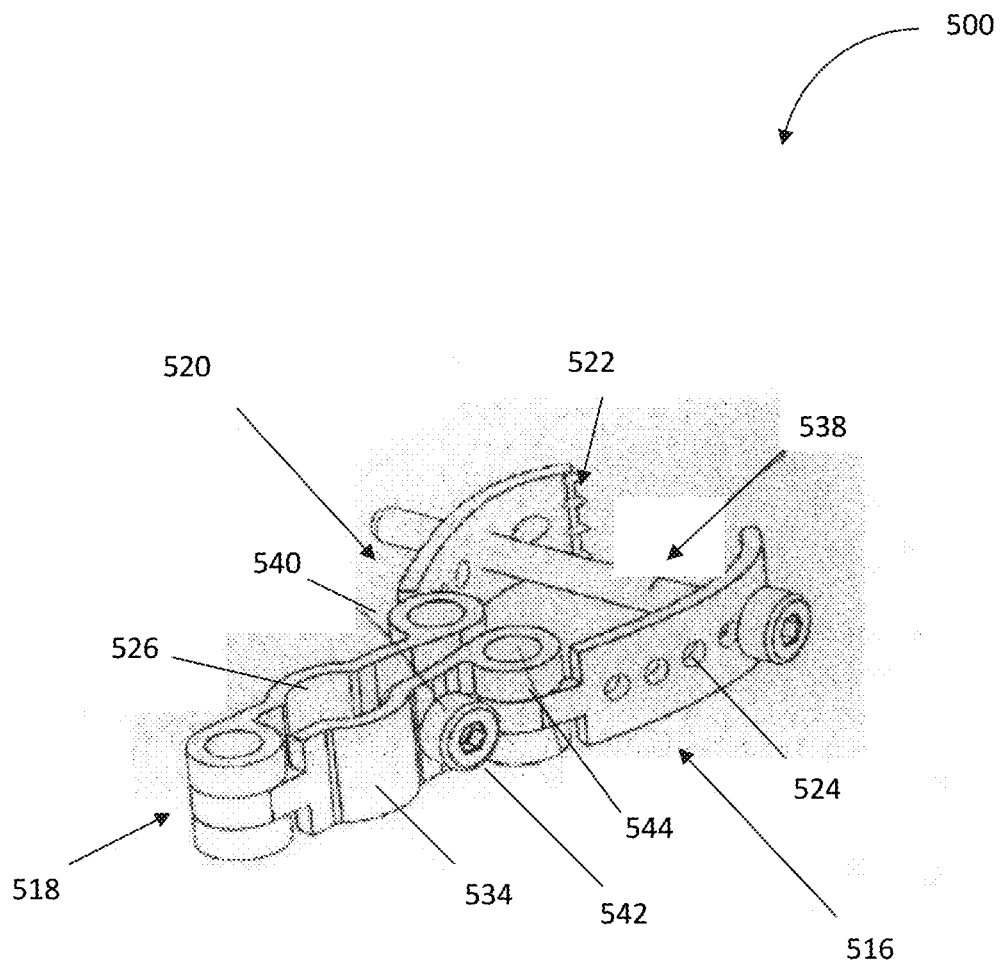
FIG. 5 shows another embodiment of the device comprising of three hinges.

FIG. 5 shows another embodiment of the device 500 comprising of a first hinge 540, a second hinge 544, and a third hinge 518. Two hinges 540 and 544 may be positioned, for example, essentially midway along the device 500 with a single hinge 518 located posteriorly.

One of each of the first hinge 540 and the second hinge 544 may be positioned along the length of one of the first pivoting arm 516 and the second pivoting arm 520 respectively, creating a second pivot point for each of the first pivoting arm 516 and the second pivoting arm 520. That is, the first pivoting arm 516 and the second pivoting arm 520 will be able to pivot around the single posterior hinge 518, and, additionally, each of the first pivoting arm 516 and the second pivoting arm 520 will have another hinge along their length that will create a second pivot point.

For example, if the first hinge 540 and the second hinge 544 are each respectively located midway along the length of the first pivoting arm 516 and the second pivoting arm 520, each of the first pivoting arm 516 and the second pivoting arm 520 would be able to also pivot around its second hinge. This feature is advantageous, because, for example, it allows for pivoting in each of the first pivoting arm 516 and the second pivoting arm 520 when pivoting around the posterior hinge 518 is prevented. Pivoting around the posterior hinge 518 may be prevented when the device 500 attaches to a multi-level rod.

The distal portion of the embodiment shown in FIG. 5, comprises a component for engaging with a multi-level rod. Two concave segments 526 and 543 are positioned along the distal portions of the first pivoting arm 516 and the second pivoting arm 520. The two concave segments 526 and 534 may preferably be positioned between the posterior hinge 518 and the two proximal hinges 540 and 544, but other positions relative to the three hinges 518, 540, and 544 are possible. The first concave segment 526 and the second concave segment 534 are sized to tightly wrap around the multi-level rod. The first concave segment 526 and the second concave segment 534 may be separated or brought together when the first pivoting arm 516 and the second pivoting arm 520 are pivoted around the posterior hinge 518.

A locking mechanism 542 may be present for tightly securing the first concave segment 526 and the second concave segment 534 around a multi-level rod. The locking mechanism 542 may comprise a threaded rod that engages with a threaded opening or opening located between the concave segments and the anterior hinges. The engaging of the threaded rod with the threaded opening tightly brings the first pivoting arm 516 and the second pivoting arm 520 together thus tightly locking the first concave segment 526 and the second concave segment 534 around a multi-level rod. Alternative methods for a locking mechanism exist. Non-limiting examples of a locking mechanism may include a clip or alternatively a tie that is placed over the first pivoting arm 516 and the second pivoting arm 520 in such a way that the clip or tie tightly brings the first pivoting arm 516 and the second pivoting arm 520 together.

In an embodiment, the device 500 comprises a single concave segment, which secures the multi-level rod as, for example, described elsewhere herein.

Bringing the first pivoting arm 516 and the second pivoting arm 520 tightly together with the locking mechanism 542 typically will prevent further pivoting around the posterior hinge 518. The first hinge 540 and the second hinge 544, however, continue to allow pivoting. Specifically, the portions of the first pivoting arm 516 and the second pivoting arm 520 that are proximal to the first hinge 540 and the second hinge 544 may pivot around their respective anterior hinges. This is advantageous because, for example, the fixation of the multi-level rod, through attachment to the multi-level rod, may occur independently of the fixation of the device 500 to the vertebral facet joint.

It should be understood that the embodiment shown in FIG. 5 further comprises of features already described herein that function in a similar manner to the previously described features. For example, the device 500 comprises at least one retaining element 522 positioned at the proximal end of the device 500, wherein the at least one retaining element 522 assists in securing or fixing the device 500 to the surface of a vertebral facet. The retaining elements 522 may transiently or reversibly secure the device 500 to a vertebral facet when the first pivoting arm 516 and the second pivoting arm 520 of the device 500 are closed around the facet joint, but the device 500 has not yet been fixed to the vertebral facet joint. For example, the first pivoting arm 516 and the second pivoting arm 520 of the device 500 each also comprise at least one opening 524 or opening preferably in their proximal aspect. The at least one opening 524 or opening may be positioned on the first pivoting arm 516 and the second pivoting arm 520 of the device 500 so that the opening 524 or the first pivoting arm 516 and the second pivoting arm 520 is positioned essentially directly across from the opening 524 or opening in the other arm.

Figure 6:
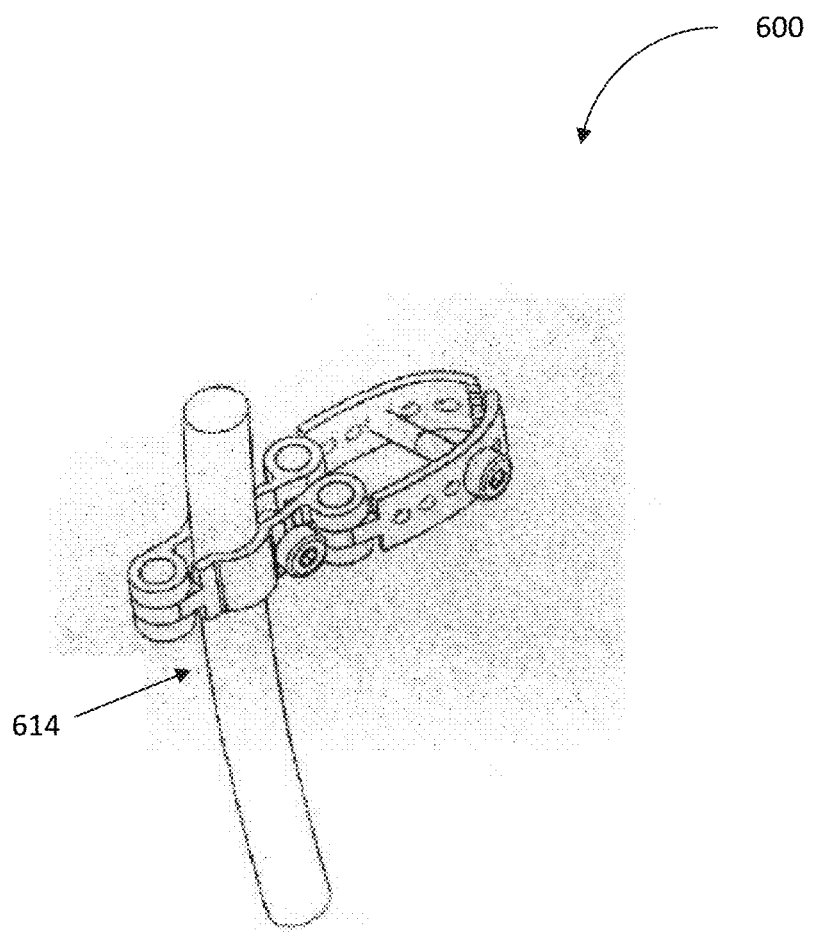
FIG. 6 shows an embodiment of the device engaging with a multi-level rod.

FIG. 6 shows device 600, the embodiment of FIG. 5, as it may engage with a multi-level rod 614.

For example, referring again to FIG. 5, the first pivoting arm 516 and the second pivoting arm 520 may be opened or separated by pivoting around the posterior hinge 518, thereby separating the concave segments 526 and 534.

A multi-level rod 614 may be engaged by concave segments 526 and 534 by, for example, closing or bringing together the first pivoting arm 516 and the second pivoting arm 520 so that the concave segments wrap around or encircle the multi-level rod 614. A tight engagement may be achieved by engaging the locking mechanism 542 to bring concave segments 526 and 534 together tightly around the multi-level rod 614. The portion of the first pivoting arm 516 and the second pivoting arm 520 that are proximal to the proximal first 540 and second 544 hinges may then be positioned around a vertebral facet joint and fixed into position by the methods described herein.

It should be understood that the embodiments shown in FIG. 6 further comprise of features already described herein that function in a similar manner. For example, the device 600 comprises of a plurality of retaining elements positioned at the proximal end of the device 600, wherein the retaining elements assist in securing or fixing the device 600 to the vertebral facet. The retaining elements may transiently or reversibly secure the device 600 to a vertebral facet when the arms of the device 600 are closed around the facet, but the device 600 has not yet been fixed to the vertebral facet. For example, the pivoting arms of the device 600 each also comprise at least one opening or opening preferably in their proximal aspect. The at least one opening or opening may be positioned on each pivoting arm of the device 600 so that the opening or opening on each arm is positioned essentially directly across from the opening or opening in the other arm.

Figure 7:
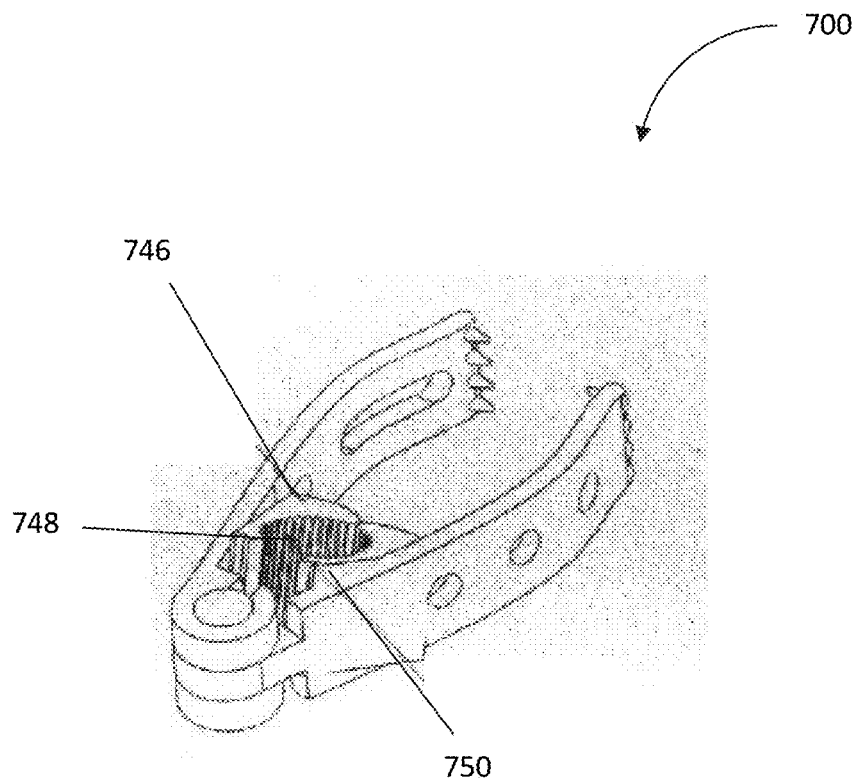
FIG. 7 shows an embodiment wherein the concave segments rotate around an axis.

FIG. 7 shows an embodiment wherein the concave segments 746 and 750 articulate or rotate around an axis 748. In this embodiment, the concave segments 746 and 750 are not contiguous with or incorporated into the pivoting arms. Rather the concave segments that are positioned along the pivoting arms may each be separate components that are attached to the pivoting arms at a single point that allows for free rotation. For example, each concave segment 746 and 750 may be a part of a separate component that attaches to the pivoting arms.

The separate component comprising concave segments 746 and 750 may, for example, have an opening on a surface opposite the concave segments 746 and 750 that may engage with a protrusion or short rod on the pivoting arm so that the separate component comprising concave segments 746 and 750 rotates around an axis that is horizontal to the device 700. That is, the separate component rotates around the axis formed by the protrusion or short rod around which the component rotates like a wheel.

The protrusion or short rod may not penetrate through the entire separate component so that concave segments 746 and 750 remain intact. It should be understood that the protrusion or short rod may be attached instead to the separate component, which may engage an opening on the pivoting arms. It should also be understood that a rotatable connection between the separate component and the pivoting arms may be achieved in other ways such as, for example, with the use of a bolt.

It should be understood that the embodiment shown in FIG. 7 further comprises of features already described herein that function in a similar manner. For example, the device 700 comprises of at least one retaining element positioned at the proximal end of the device 700, wherein the retaining element assists in securing or fixing the device 700 to the vertebral facet. The retaining elements may transiently or reversibly secure the device 700 to a vertebral facet when the arms of the device 700 are closed around the facet, but the device 700 has not yet been fixed to the vertebral facet. For example, the pivoting arms of the device 700 each also comprise at least one opening or opening preferably in their proximal aspect. The at least one opening or opening may be positioned on each pivoting arm of the device 700 so that the opening or opening on each arm is positioned essentially directly across from the opening or opening in the other arm.

Figure 8:
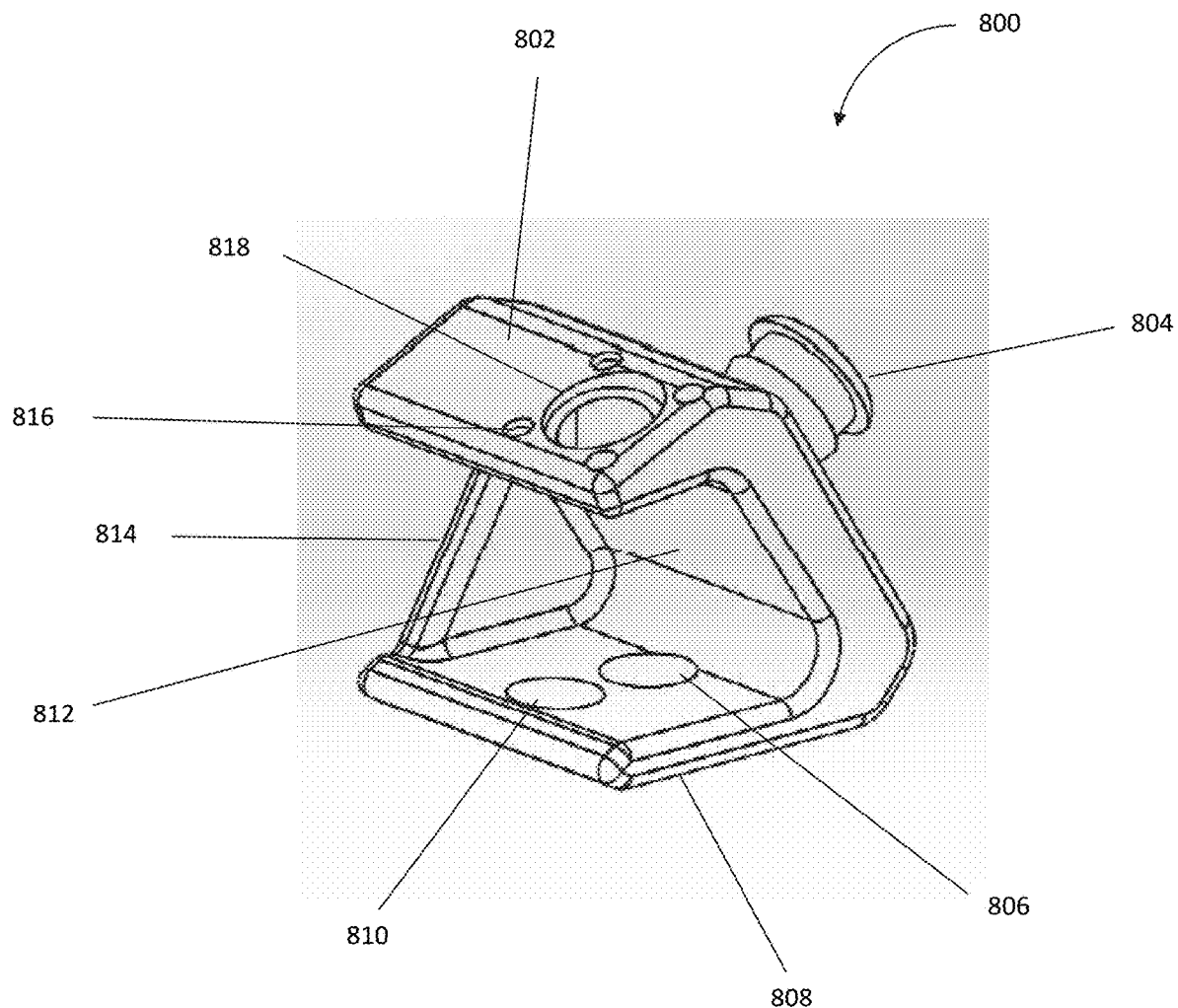
FIG. 8 shows an embodiment of a vertebral fixation device that is configured to couple with a vertebral facet joint and fix a superior facet to an inferior facet.

FIG. 8 shows an embodiment of a vertebral fixation device 800 that is configured to securely couple with a vertebral facet joint. In an embodiment, a vertebral fixation device 800 comprises a superior wall 802, an inferior wall 808, and a posterior wall 812. A superior wall 802, an inferior wall 808, and a posterior wall 812 may be configured to form a recess within the vertebral fixation device 800. A recess within the vertebral fixation device 800 may be configured to receive a facet joint or an individual facet within the recess. In an embodiment, the vertebral fixation device 800 may be C-shaped, wherein the C-shape is formed from the superior wall 802, the inferior wall 808, and the posterior wall 812. It should be understood that other shapes are suitable with the devices, systems, and methods described herein including, for example, a vertebral fixation device comprising a V-shape or a U-shape. In an embodiment, at least a portion of a superior wall 802 is essentially parallel to at least a portion of an inferior wall 808. In an embodiment, at least a portion of a superior wall 802 and/or at least a portion of an inferior wall 808 are angled. In an embodiment, at least a portion of a superior wall 802 and/or at least a portion of an inferior wall 808 are angled towards each other and define an angle in space that is created by the intersection of a line that extends out from the angled portion of the superior wall 802 and a line that extends from the angled portion of the inferior wall 808. In an embodiment, the intersection of the line that extends from an angled portion of a superior wall 802 and a line that extends form an inferior wall 808 forms an angle in space that equals 65 degrees. In an embodiment, the intersection of a line that extend from a superior wall 802 and a line that extends form an inferior wall 808 forms an angle in space that equals 60 degrees. In an embodiment, the intersection of a line that extend from a superior wall 802 and a line that extends form an inferior wall 808 forms an angle in space that equals 55 degrees. In an embodiment, the intersection of a line that extend from a superior wall 802 and a line that extends forms an inferior wall 808 form an angle in space that equals 50 degrees. In an embodiment, the intersection of a line that extend from a superior wall 802 and a line that extends forms an inferior wall 808 form an angle in space that equals 45 degrees. In an embodiment, the intersection of a line that extend from a superior wall 802 and a line that extends form an inferior wall 808 forms an angle in space that equals 40 degrees. In an embodiment, the intersection of a line that extend from a superior wall 802 and a line that extends form an inferior wall 808 form an angle in space that equals 30 degrees. In an embodiment, at least a portion of a superior wall 802 is directed away from at least a portion of an inferior wall 808.

In an embodiment, a vertebral fixation device 800 further comprises a lateral wall 814. A lateral wall 814, may be a partial wall (as shown) or a complete wall that covers an entire lateral side of the device 800. In FIG. 8, the lateral wall 814 is positioned on a right lateral side of the device 800 as shown. In another embodiment, a lateral wall is positioned on a left lateral side of the device 800. The lateral wall 814 functions to further enclose the recess within the device 800 to help form a better fit with a facet joint. The embodiment comprising a right lateral wall 814 (shown) is configured to couple with a right facet joint, whereas an embodiment comprising a left lateral wall (not shown) is configured to couple with a left facet joint. In an embodiment, a vertebral fixation device 800 comprises either a right lateral wall 814 or a left lateral wall. A vertebral fixation device 800 comprising a right lateral wall 814 is a right vertebral fixation device 800 and a vertebral fixation device with a left lateral wall is a left vertebral fixation device. In an embodiment, a lateral wall 814 functions as a shield or positioning-stop to, for example, aid in the proper positioning of the vertebral fixation device 800 and to, for example, aid in forming a tight coupling between a right and left facet joint and a right and left vertebral fixation device.

In an embodiment, a vertebral fixation device 800 comprises features that create a tight coupling with a facet joint. In an embodiment, an inferior wall 808 to be positioned between to facets that form a facet joint. That is, in this embodiment, during a spinal fixation procedure the recess in the vertebral fixation device 800 receives a superior facet when the inferior wall 808 is inserted between the superior facet and an inferior facet that form a facet joint. In practice, an inferior wall of a vertebral fixation device 800 may fit directly between two facets or a space may have to first be created using, for example, standard orthopedic tools such as a bone file or rasp to create the space between the two facets for the inferior wall 808 to enter. In an embodiment, a right and left lateral walls 814 of a first and a second vertebral fixation device 800 are respectively positioned around the lateral sides of a right (right lateral wall of first vertebral fixation device 800) vertebral facet and a left vertebral facet (left lateral wall of first vertebral fixation device). In this embodiment, the right and left lateral walls may be used to apply a horizontal compression across the spine by, for example, connecting two vertebral fixation devices 800 together with tension. In this embodiment, two vertebral fixation devices 800 may be connected to create a horizontal compression of the spine by, for example, using a horizontal rod that is secured between the vertebral fixation devices 800 while the two devices 800 are held under lateral tension. A lateral tension may be applied to the respective lateral walls 814 during a spinal fixation procedure by, for example, a clamp-like tool that grasps and presses on both lateral walls of two vertebral fixation devices 800 while the devices 800 are coupled to vertebral facet joints, or, for example, by the hands of the surgeon compressing the two devices 800 towards each other with a pinching action. In this embodiment, connecting the two vertebral fixation devices 800 together with a cross-connector, as described herein, while the two devices 800 are laterally compressed fixes the two devices 800 together under the force of the lateral tension, which is applied to the respective vertebral facets and thus the lateral compression is applied to the spine. The application of lateral compression to the spine through the facet joints is advantageous in that, for example, it contributes to the formation of a tight coupling between the vertebral fixation device 800 and the vertebral facet joints. A tight coupling between a vertebral facet and a vertebral fixation device 800 promotes osteointegration of the device 800. Osteointegration may be further promoted by roughening the surfaces of a vertebral fixation device 800 that are configured to couple with bone. In an embodiment, a vertebral fixation device 800 comprises roughened surfaces that are configured to promote osteointegration.

In an embodiment, vertebral fixation device 800 further comprises a first opening 818, a second opening 806, and optionally a third opening 810. A first opening 818 goes through the superior wall 802 of a vertebral fixation device 800, and a second opening 806 goes through the inferior wall 808 of a vertebral fixation device 800. The first 818 and second 806 openings are positioned so that a screw may be passed through the first opening 818 and into the second opening 806 at a first angle. In an embodiment, a third opening 810 is positioned through the inferior wall 808 that a screw may be passed through the first opening 818 and through the third opening 810 at a second angle. When used in a fixation procedure, a screw is passed through the first opening 818 of the vertebral fixation device 800, pass through a vertebral facet joint, and then pass through either a second opening 806 or alternatively to pass through a third opening 810 in an embodiment comprised of three openings.

Figure 15:
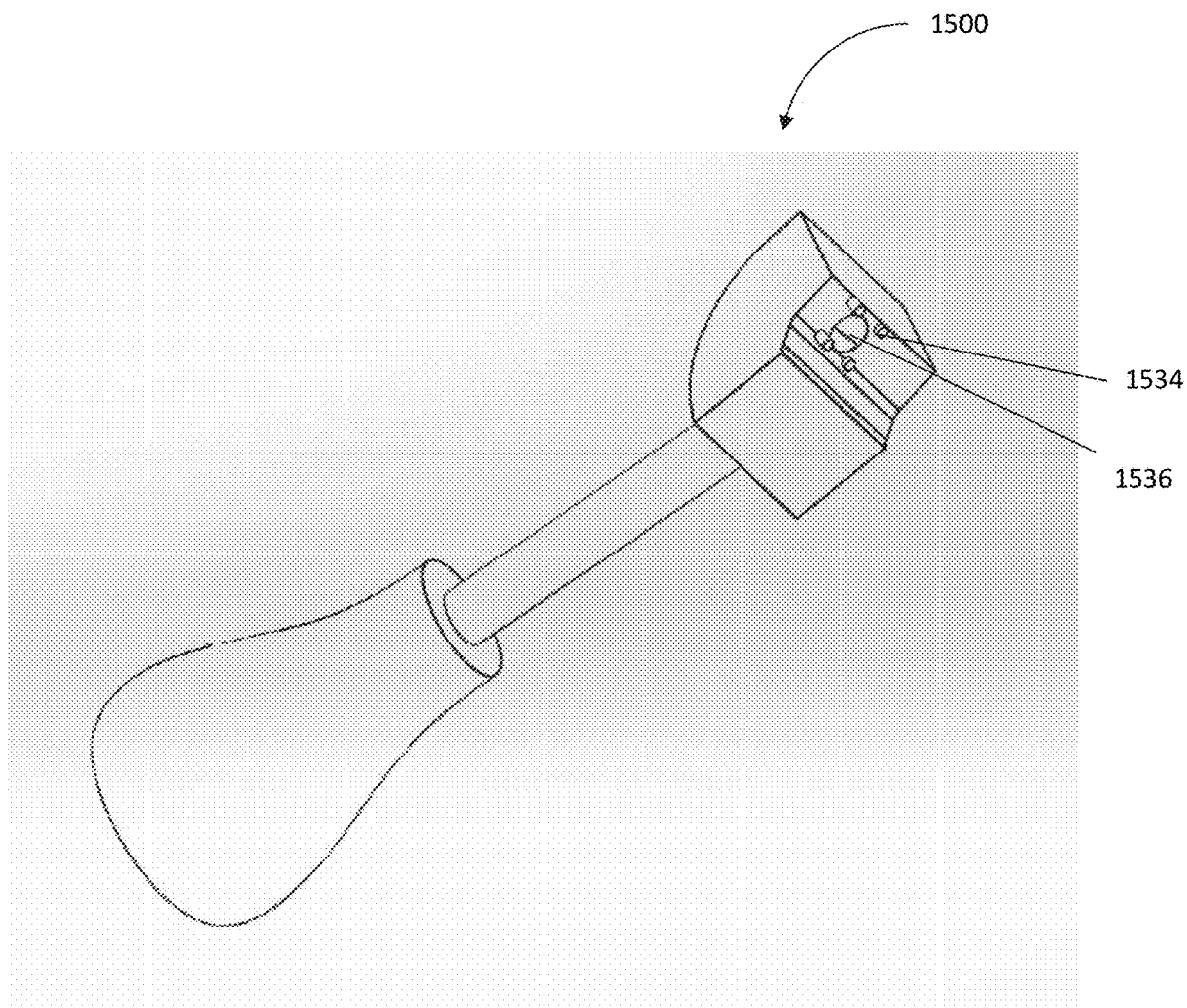
FIG. 15 shows an inferior view of an embodiment of a drill guide as described herein.
Figure 16:
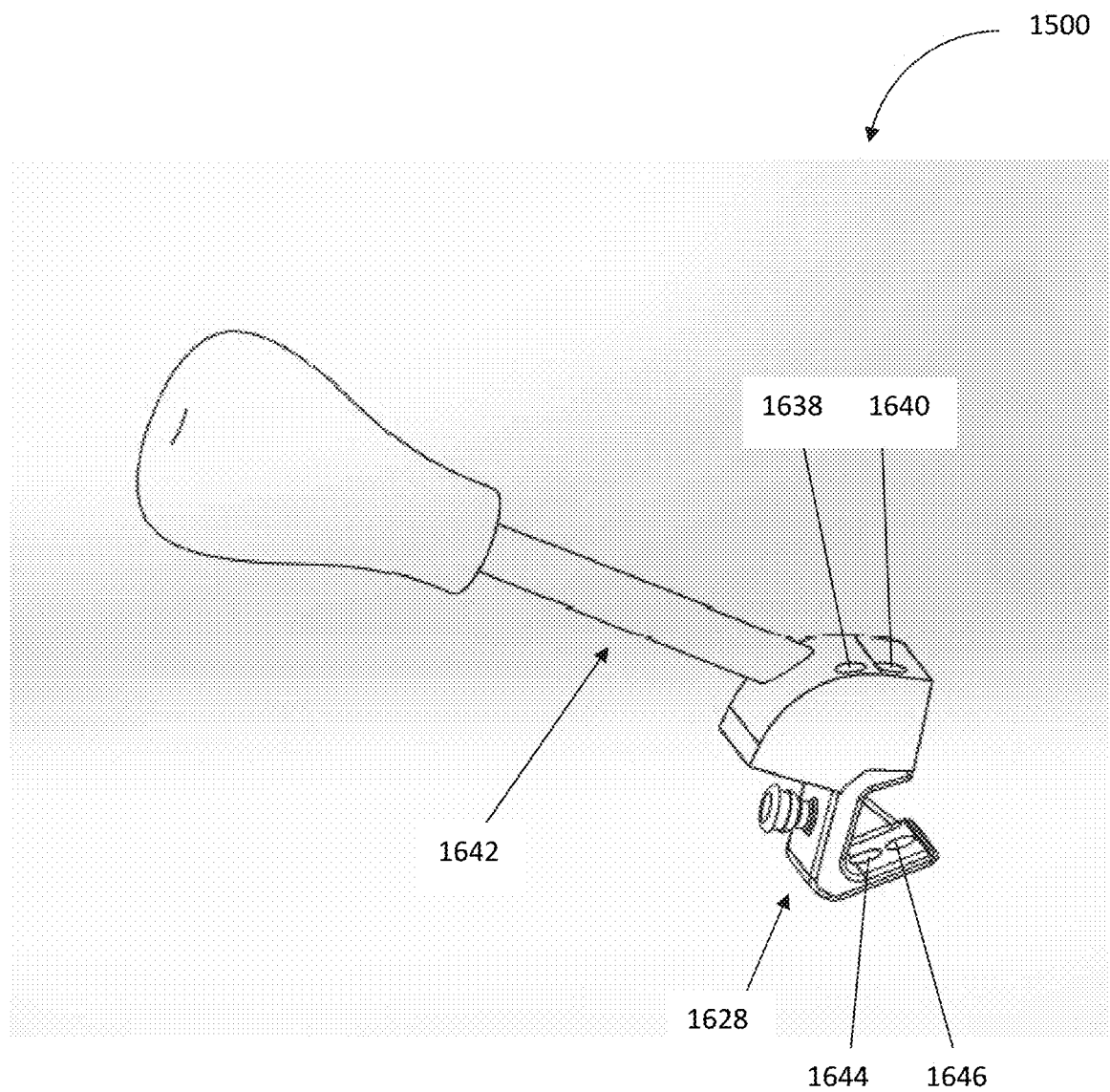
FIG. 16 shows a superior view of an embodiment of a drill guide coupled with vertebral fixation device.

The user is guided to angle the screw through either a second 806 or a third opening 810 by a drill guide tool (as shown in FIGS. 15 and 16). It should be understood that embodiments comprising two or more openings are consistent with the devices, systems, and methods described herein, including devices with one or more openings through a superior wall 802 and devices with one or more openings through an inferior wall 808. A superior wall 802 and/or an inferior wall 808 may comprise, for example, 6 openings. A superior wall 802 and/or an inferior wall 808 may comprise, for example, 5 openings. A superior wall 802 and/or an inferior wall 808 may comprise, for example, 4 openings. A superior wall 802 and/or an inferior wall 808 may comprise, for example, 3 openings. A superior wall 802 and/or an inferior wall 808 may comprise, for example, 2 openings. A superior wall 802 and/or an inferior wall 808 may comprise, for example, 1 opening.

In an embodiment, a screw is passed through a first opening 818, a vertebral facet, and through a second opening 806 or a third opening 810. In an embodiment, the inferior wall 808 is raised up by the, for example, threading in the screw so that the device 800 tightly cinches to the vertebral facet joint. The action of a threaded screw in passing through and embedding in the inferior facet may lift the inferior facet and cinch it to the inferior wall of the vertebral fixation device 800. In an embodiment, a screw is passed through a first opening 818 and through a second opening 806 of the vertebral fixation device 800 while the inferior wall 808 of a vertebral fixation device 800 is positioned between a superior and an inferior facet and the vertebral fixation device 800 is positioned to receive a superior vertebral facet within a recess in the vertebral fixation device 800. In an embodiment, a screw passes through the superior facet of the facet joint when the screw is passed through the first 818 and third 810 openings and the vertebral fixation device 800 is positioned to receive an inferior vertebral facet within a recess in the vertebral fixation device 800. In an embodiment, when an inferior wall 808 of a vertebral fixation device 800 is positioned between a superior and inferior facet of a facet joint a screw is passed through a first opening 818 and a third opening 810 opening, and the screw comprises a length that allows for the screw to pass beyond the third opening 810 and into the inferior facet of the facet joint. In this embodiment, a screw passes through a superior facet within the recess of the vertebral fixation device 800 and into an inferior facet directly beneath the inferior wall 808 of the vertebral fixation device 800. In an embodiment, threading in the screw may act to cinch the inferior facet against the inferior wall of the vertebral fixation device 800 that is positioned within the facet joint (i.e. between the superior and inferior facets) as described.

Figure 10:
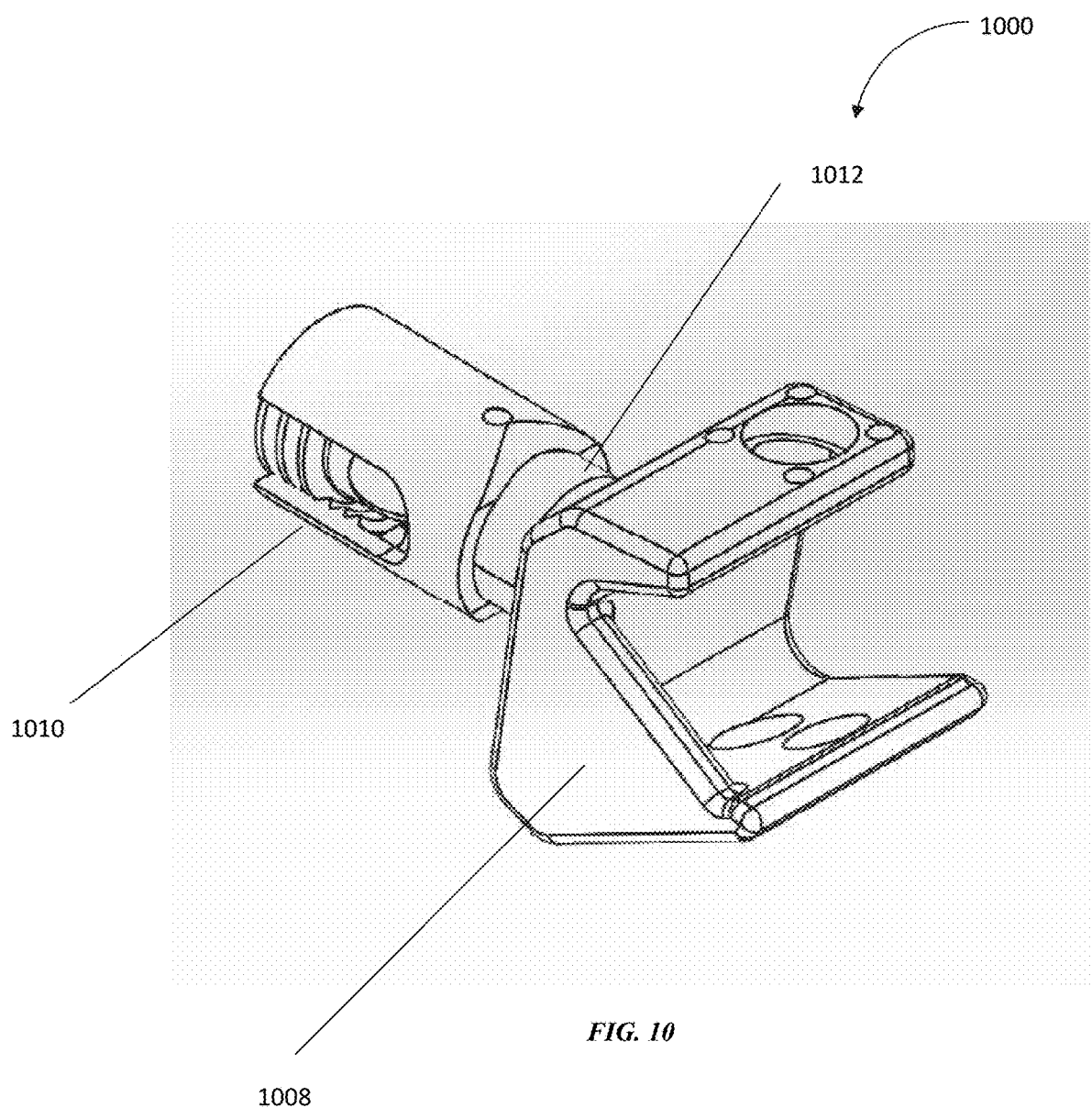
FIG. 10 shows an oblique view of a vertebral fixation device that is coupled with an articulating coupler.
Figure 12:
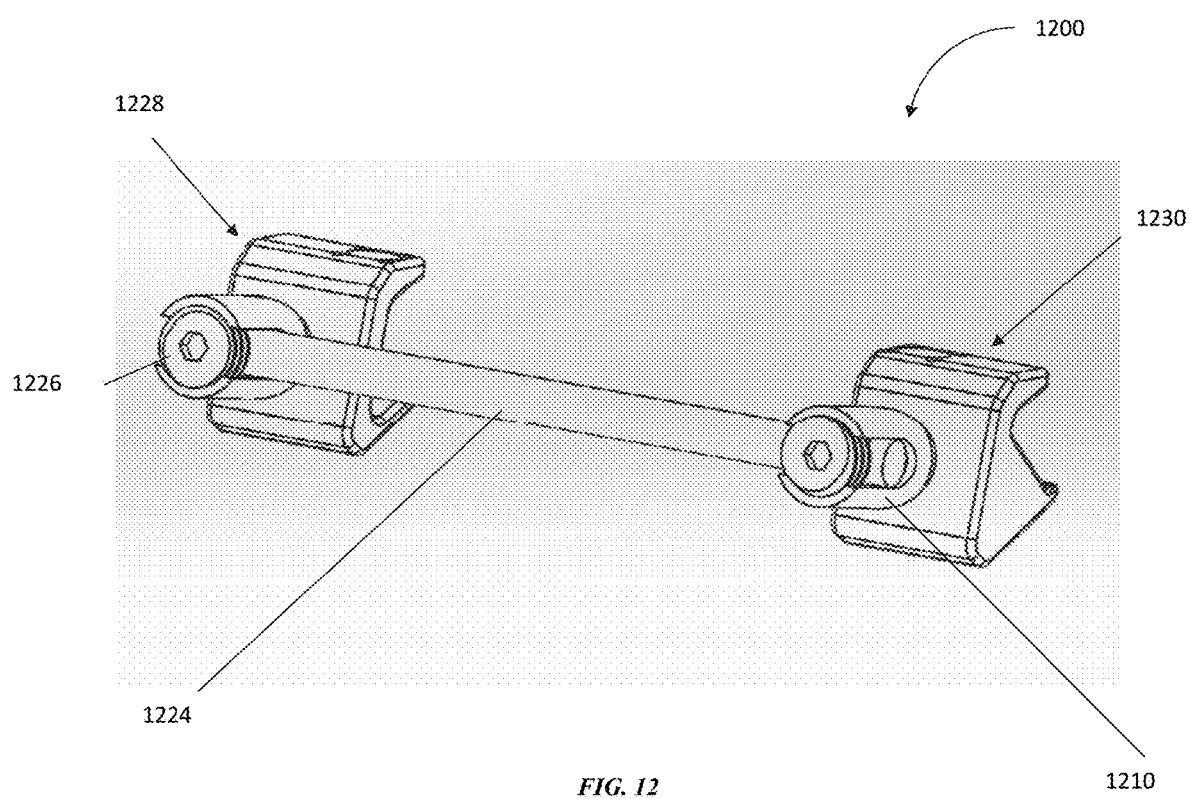
FIG. 12 shows a posterior view of an embodiment of a single level vertebral fixation system as described herein.
Figure 13:
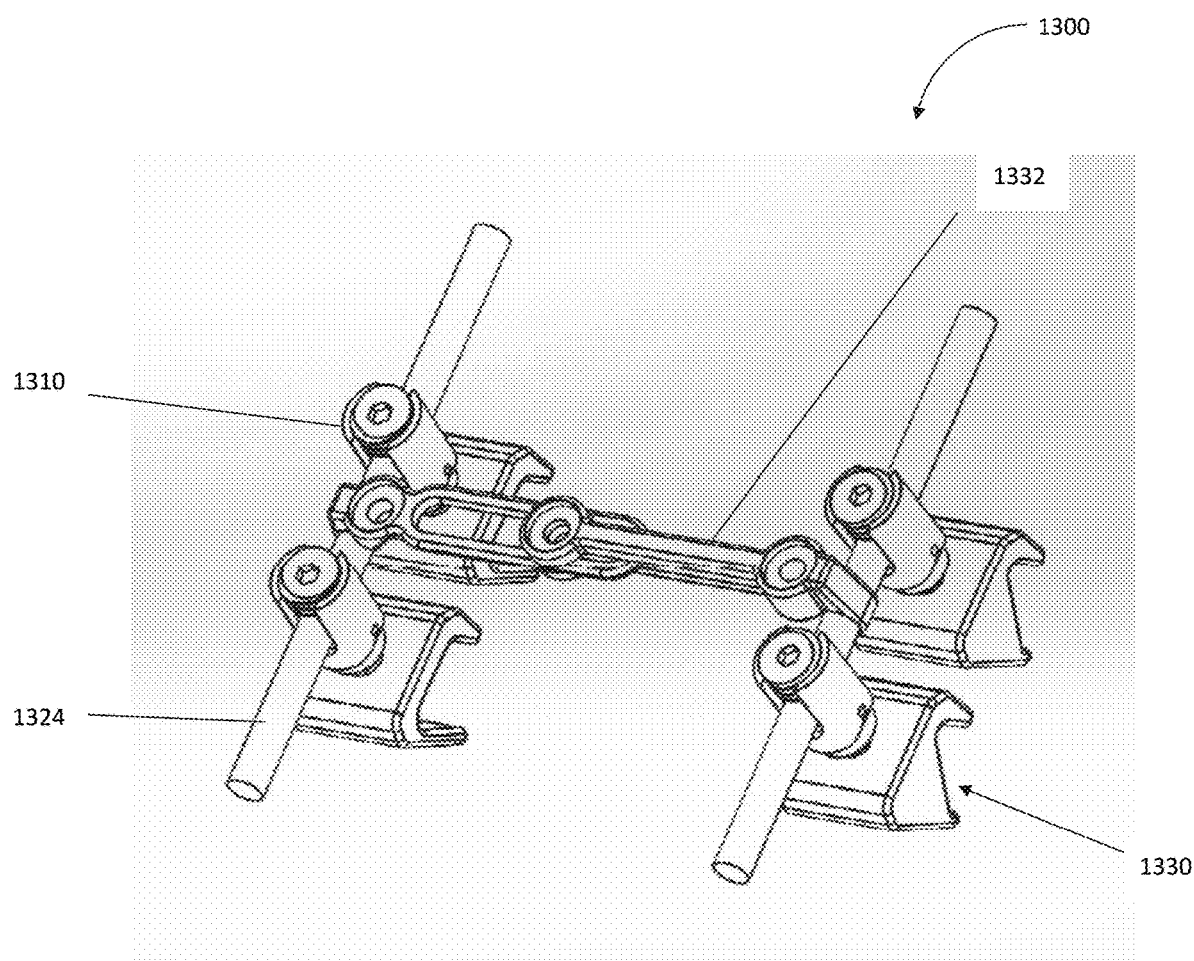
FIG. 13 shows a posterior view of an embodiment of a multi-level vertebral fixation system as described herein.
Figure 14:
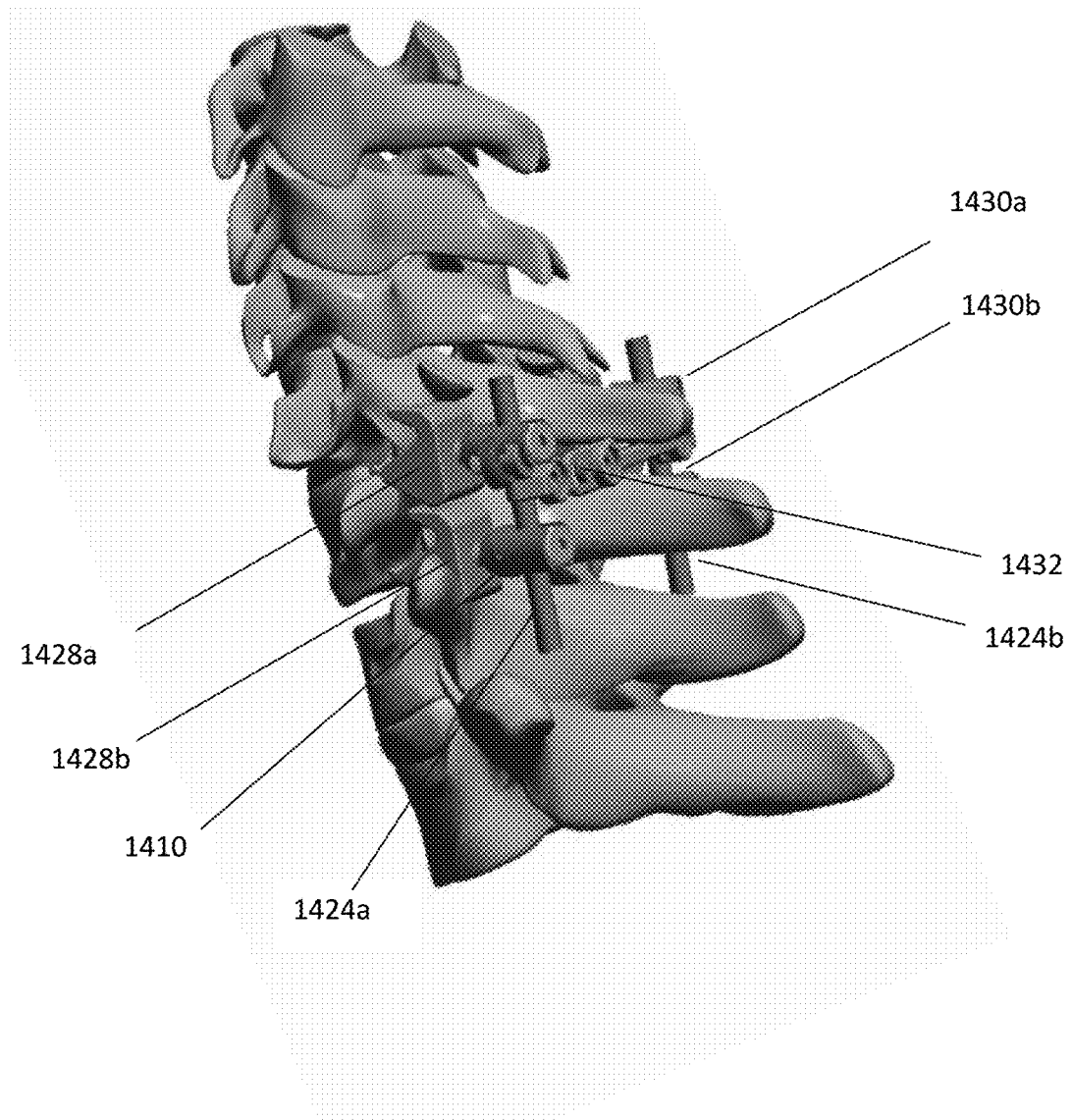
FIG. 14 shows an embodiment of a multi-level vertebral fixation system fixed to the spine in accordance with the description herein.

In an embodiment, a vertebral fixation device 800 further comprises a pin 804 that is positioned on a posterior wall 812 of the device 800. The pin 804 functions to couple the device 800 to a horizontal rod (as shown in FIGS. 12-14). In an embodiment, a pin couples with an articulating coupler (as shown in FIG. 10). A horizontal rod may function to interconnect multiple vertebral fixation devices 800 together. In an embodiment, a horizontal rod couples with a pin 804 to connect a right vertebral fixation device 800 that is fixed to a right facet joint as described herein with a left vertebral fixation device 800 that is fixed to a left facet joint as described herein, wherein both vertebral fixation devices 800 are fixed at the same vertebral level. In an embodiment, a horizontal rod couples with a pin 804 to connect a first device 800 fixed at a first vertebral level with a second device 800 fixed at a second vertebral level. That is, in an embodiment, a horizontal rod connects vertebral devices 800 that are fixed to multiple facets on an ipsilateral side of the spine.

In an embodiment, a pin 804 is configured to couple with an articulating coupler (as shown in, for example, FIG. 10). A pin 804 may be essentially spherical in shape or ball shaped so that an articulating coupler receives the spherical shape within an opening in the articulating coupler, forming a coupling essentially similar to a ball and socket joint. The coupling of the articulating coupler with the pin 804 provides a joint configured for essentially polyaxial movement around the pin 804. It should be understood that other coupling mechanisms that allow a pin 804 to couple with an articulating coupler are suitable for use with the devices, systems, and methods described herein, and may allow an articulating coupler that is coupled to a pin 804 to articulate polyaxially around the pin 804.

In an embodiment, an articulating coupler couples with a horizontal rod. In an embodiment, a horizontal rod couples with an articulating coupler to connect a right vertebral fixation device 800 fixed to a right facet joint with a left vertebral fixation device 800 fixed to a left facet joint at the same vertebral level. In an embodiment, a vertical rod couples with an articulating coupler to connect a first device 800 fixed at a first vertebral level with a second device 800 fixed at a second vertebral level.

In an embodiment, a drill guide coupler 816 is positioned on a superior wall 802. A drill guide coupler 816 is configured to removably couple with a drill guide as, for example, shown in FIG. 15. In an embodiment, one or more drill guide couplers 816 comprise indentations in a superior wall 802, and are configured to receive an equal number of protrusions in a drill guide. FIG. 8 shows an exemplary embodiment in which four drill guide couplers 816 comprise four indentations arranged in a square pattern around a first opening 818. In the exemplary embodiment, a drill guide with four protrusions is configured fit directly into the four drill guide couplers 816 to properly align a screw to be placed through the drill guide and into the first opening 818.

The vertebral fixation device 800 may, for example, measure about 1 cm in total length. Alternatively, the device 800 may, for example, measure about 1.25 cm in total length. Alternatively, the device 800 may, for example, measure about 1.5 cm in total length. Alternatively, the device 800 may, for example, measure about 1.75 cm in total length. Alternatively, the device 800 may, for example, measure about 2 cm in total length. Alternatively, the device 800 may, for example, measure about 2.25 cm in total length. Alternatively, the device 800 may, for example, measure about 2.5 cm in total length. Alternatively, the device 800 may, for example, measure about 2.75 cm in total length. Alternatively, the device 800 may, for example, measure about 3 cm in total length. Alternatively, the device 800 may, for example, measure about 3.25 cm in total length. Alternatively, the device 800 may, for example, measure about 3.5 cm in total length. Alternatively, the device 800 may, for example, measure about 3.75 cm in total length. Alternatively, the device 800 may, for example, measure about 4 cm in total length. Alternatively, the device 800 may, for example, measure about 4.25 cm in total length. Alternatively, the device 800 may, for example, measure about 4.5 cm in total length. Alternatively, the device 800 may, for example, measure about 4.75 cm in total length. Alternatively, the device 800 may, for example, measure about 5 cm in total length. Various different lengths may, for example, be suitable for use in different patients, as vertebral anatomy and vertebral size vary from patient to patient. Alternatively, longer devices may be used in combination with shorter devices in the same patient to, for example, adjust for a curvature in patient's spine that affects the alignment of the vertebrae in the vertebral column.

Suitable material for forming the device 800 includes durable metals such as, for example, titanium or steal.

Figure 9:
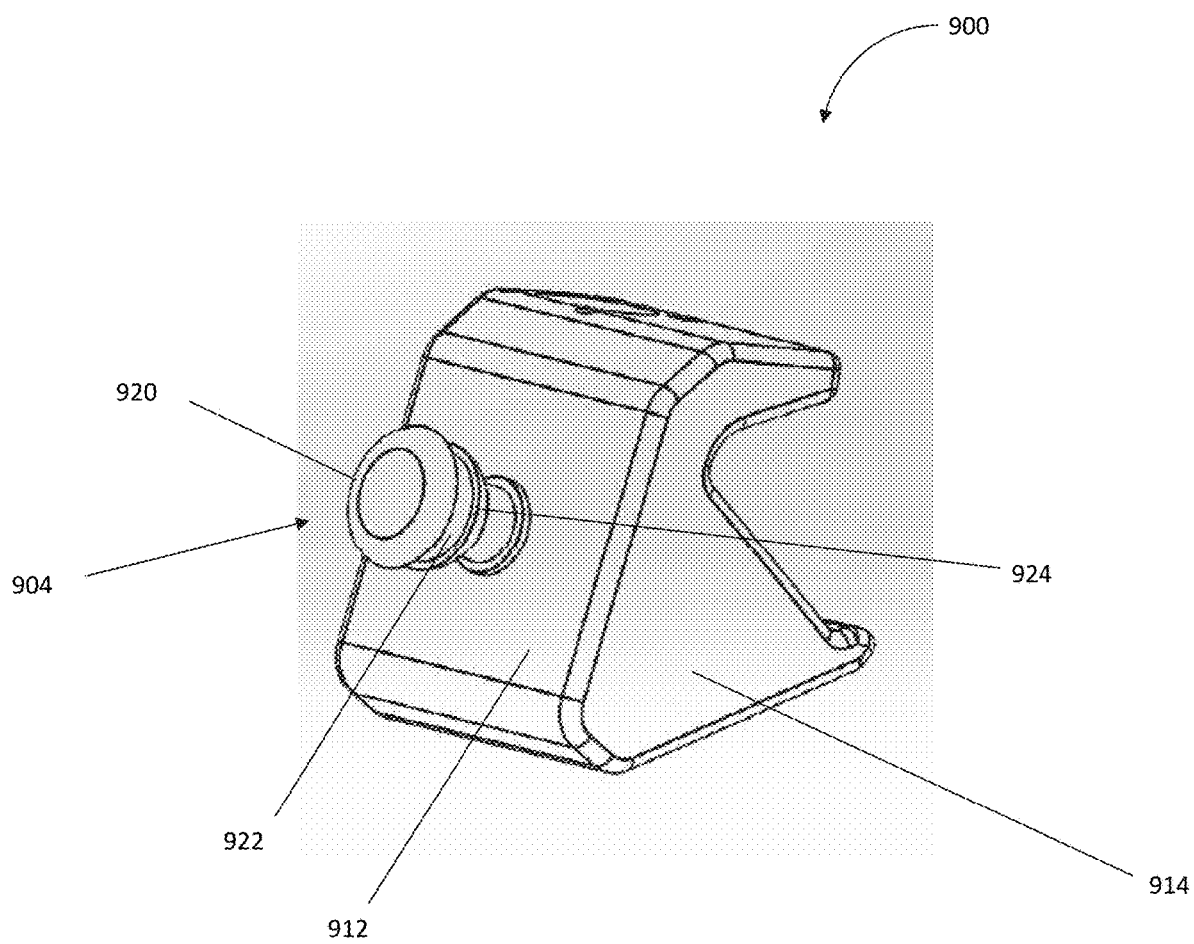
FIG. 9 shows a posterior oblique view of an embodiment of a vertebral fixation device as described herein.

FIG. 9 shows a posterior oblique view of an embodiment of a vertebral fixation device 900. In the embodiment shown, lateral wall 914 comprises a fully enclosing wall that fully encloses the lateral side of the device 900. That is to say, lateral wall 914 is a complete wall rather than a partial wall. Posterior wall 912 is coupled to a pin 904 that is positioned essentially in the center of the posterior wall 912. In an embodiment, pin 904 comprises an essentially spherical shape comprising rounded top 920, narrow middle 922, and bottom 924 segments. The top segment of pin 904 may comprise a convex shape. In an embodiment, the convex shape of the rounded top segment 920 may have a truncated top. The bottom segment of an essentially spherical pin 904 comprises a convex shape as well. A narrow middle segment 922 of an essentially spherical column comprises a column with a circumference that is less than the largest outer circumference of both the rounded top 920 and bottom 924 segments of the essentially spherical pin 904. In an embodiment, an articulating coupler as shown in, for example, FIG. 10 comprises an opening that is configured to fit over the rounded top segment 920 of pin 904 as well as the narrow middle segment 922 of pin 904 and lock into position there. In an embodiment, an articulating coupler is configured to be attached by a user by pressing the articulating coupler together with pin 904, and the coupling mechanism that couples pin 904 with the articulating coupler is configured so that the two components are not easily separated once coupled together. In an embodiment, the indentation of narrow middle segment 922 together with the rounded top segment 920 of pin 904 provides for space for articulation of the articulating coupler while preventing the articulating coupler from sliding forward and backwards along the length of pin 904.

In an embodiment, a ring is configured to fit around and couple together with the narrow middle segment 922. In an embodiment, the ring is positioned over the narrow middle segment 922 from the inside of the articulating coupler once the articulating coupler is coupled with the pin 904. In this embodiment, when the ring fits together with the narrow middle segment 922 from the inside of the articulating coupler, it both locks the articulating coupler into position in its coupling with pin 904 and also fits together with the narrowed middle segment 922 so that the thickness of the ring completes the essentially spherical shape of the pin 904. That is, the dimensions of the ring are such that when the ring is fit together with the narrow middle segment 922 the height of the ring is the height of the narrow middle segment 922 so that the entire middle segment 922 is covered by the ring. The dimensions of the ring are also configured to make pin 904 more spherical in shape when the ring is coupled with the narrow middle segment 922.

FIG. 10 shows an oblique view of a vertebral fixation device 1000 that is coupled with an articulating coupler 1010. The articulating coupler 1010 is configured to rotate essentially polyaxially around the point of coupling 1012 as well as articulate with the essential freedom of movement of a ball and socket joint. In an embodiment, an articulating coupler 1010 comprises a tulip as is used with the traditional pedicle screw. In an embodiment, an articulating coupler 1010 comprises a standard pedicle screw head also known as a tulip. In this embodiment, a tulip comprises a saddle 1008 and an opening to receive a rod and a means of locking the rod into the saddle 1008. A means of locking the rod into the saddle 1008 may comprise a screw that when screwed into the articulating coupler, fixes a rod within the saddle 1008 of the articulating coupler 1010.

Figure 11A:
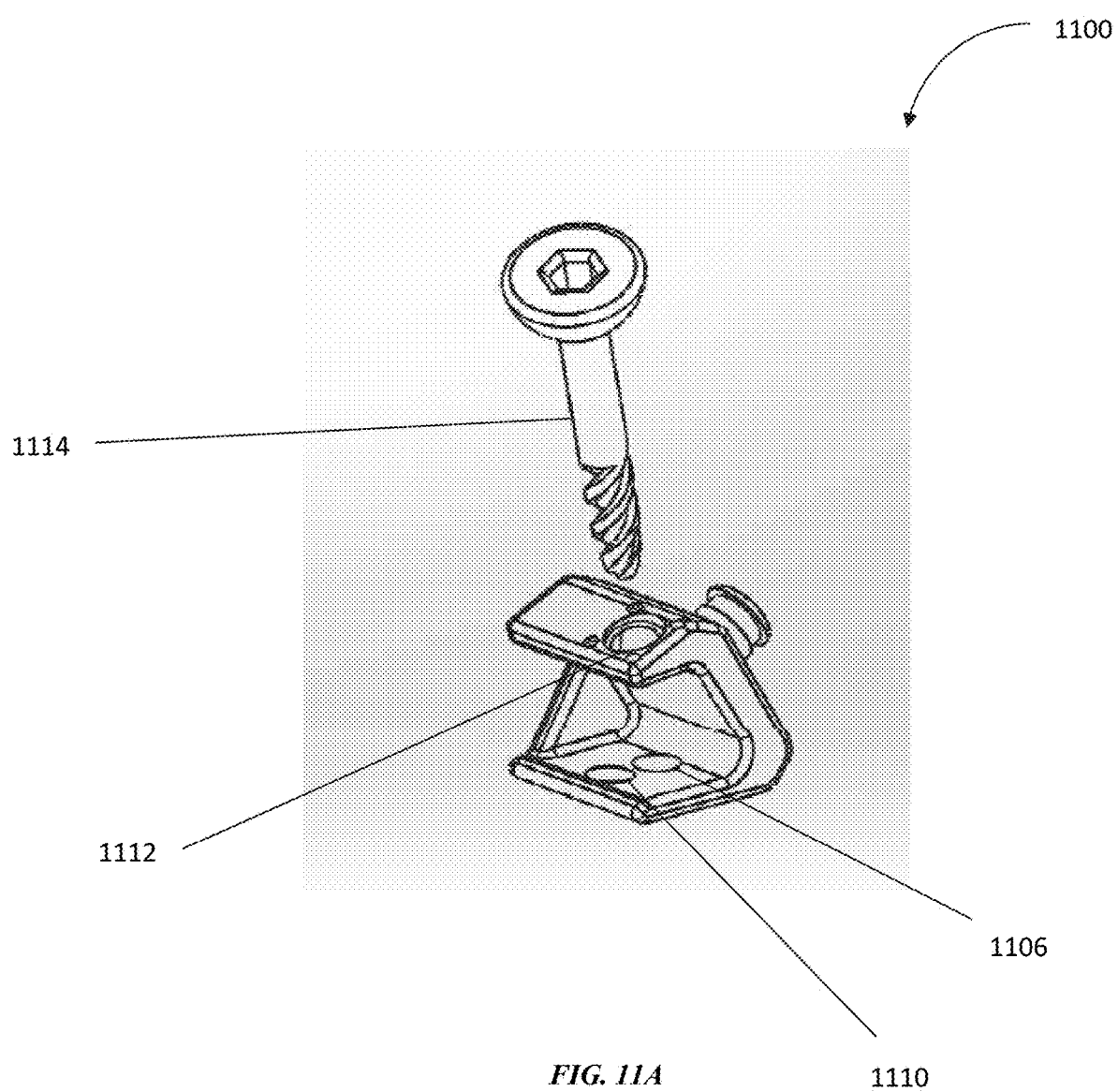
FIG. 11A shows an embodiment of a vertebral fixation device including a screw.

FIG. 11A shows an embodiment of a vertebral fixation device 1100 including a screw 1114. In the embodiment shown in FIG. 11A, screw 1114 is angled to pass through a first opening 1112 that goes through the superior wall of vertebral fixation device 1100 and pass through a second opening 1106 that goes through the inferior wall of vertebral fixation device 1100. Screw 1114 may also be angled to pass through a first opening 1112 that goes through the superior wall of vertebral fixation device 1100 and pass through a third opening 1110 that goes through the inferior wall of vertebral fixation device 1100. When used to fix two vertebrae together at a facet joint, a screw 1114 may be angled at a first angle to pass through to pass through a first opening 1112, a vertebral facet joint (not shown), and pass through a second opening 1106, or a screw 1114 may be angled at a second angle to pass through a first opening 1112, a vertebral facet joint (not shown), and pass through a third opening 1110. The ability for a user to place a screw 1114 at either of a first or second angle provides a user a greater ability to adjust to embodiments in joint anatomy from patient to patient as well as differences in the facet joints at different levels of the spine. An advantage to the vertebral fixation device 1100 is that it provides the ability to fix vertebrae using much smaller screws than the traditional large bore pedicle screws. The use of a smaller screw greatly reduces the risk of bone fracture during placement. In an embodiment, a screw 1114 is about 4 mm in its smallest diameter. In an embodiment, a screw 1114 is about 3.5 mm in its smallest diameter. In an embodiment, a screw 1114 is about 3 mm in its smallest diameter. In an embodiment, a screw 1114 is about 2.5 mm in its smallest diameter. In an embodiment, a screw 1114 is about 2 mm in its smallest diameter. In an embodiment, the widest diameter of a first opening comprises 4.5 mm. In an embodiment, the widest diameter of a first opening comprises 4 mm. In an embodiment, the widest diameter of a first opening comprises 3.5 mm. In an embodiment, the widest diameter of a first opening comprises 3 mm. In an embodiment, the widest diameter of a first opening comprises 2.5 mm. In an embodiment, the widest diameter of a first opening comprises 2 mm.

Figure 11B:
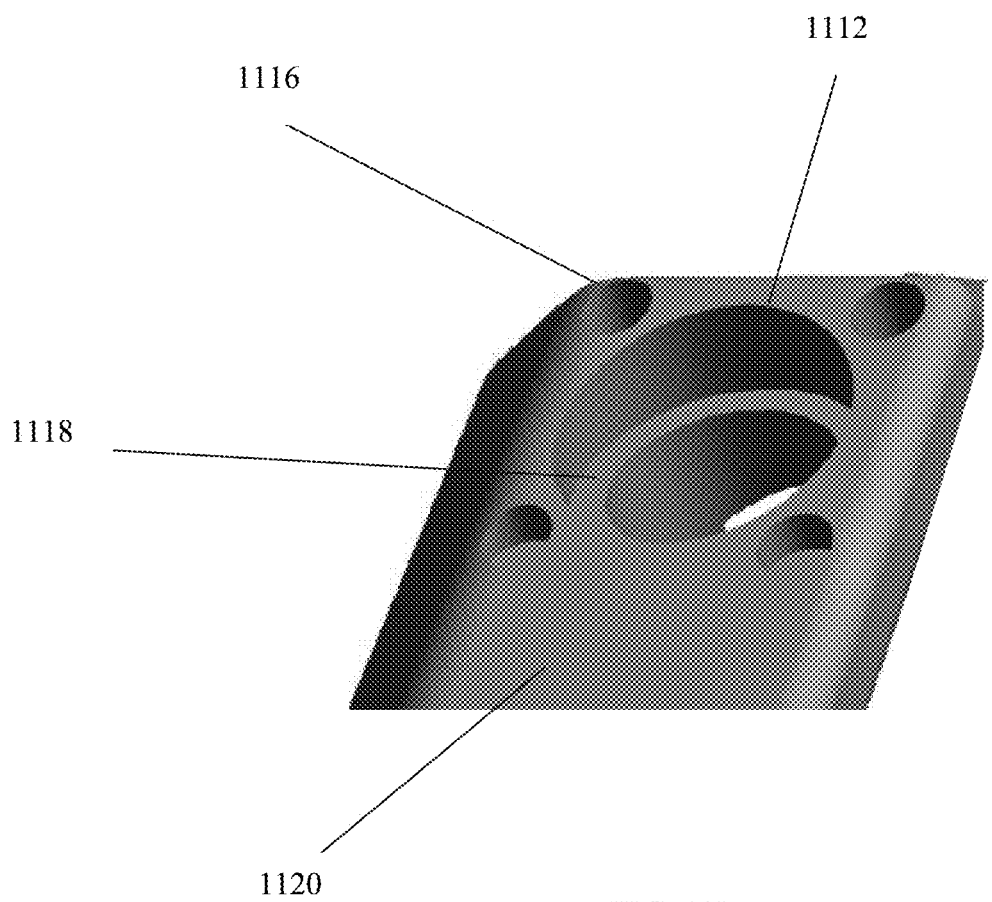
FIG. 11B shows an embodiment of an opening in a vertebral fixation device configured to receive a screw at different angles.

FIG. 11B shows an oblique view of an embodiment of a first opening 1112 on a superior wall 1120. In this embodiment, a first opening 1112 is configured to flushly seat a screw 1114 within a first opening when the screw 1114 is passed through first opening 1112 at different angles. First ridge 1118 is positioned within the first opening 1112 at an angle so that first ridge 1118 will flushly engage a screw head when screw 1114 is passed through first opening 1112 at a first angle. In an embodiment, a second ridge is positioned within first opening 1112 together with a first ridge 1118, and the two ridges are positioned to each engage a screw head when screw 1114 passes through the first opening at a different angle. The first opening 1112 may be configured to contain a plurality of ridges positioned at different angles so that the plurality of ridges are configured to engage a screw head at a plurality of corresponding different angles. One method of machining multiple ridges at different angles within a first opening is by, for example, drilling slightly offset holes at different angles so that each ridge within first opening 1112 comprises a partial circle. In an embodiment, a first opening comprises six ridges configured to flushly engage a screw at six different angles. In an embodiment, a first opening comprises five ridges configured to flushly engage a screw at five different angles. In an embodiment, a first opening comprises three ridges configured to flushly engage a screw at three different angles. In an embodiment, a first opening comprises two ridges configured to flushly engage a screw at two different angles. In an embodiment, a first opening comprises one ridge configured to flushly engage a screw at one angle. In an embodiment, one or more openings in an inferior wall of the vertebral fixation device 1100 may similarly comprise one or more ridges to receive a screw that passes through an opening through the inferior wall of a vertebral fixation device 1100. In an embodiment, a drill guide coupler 1116 is positioned on a superior wall 1120. A drill guide coupler 1116 is configured to removably couple with a drill guide as, for example, shown in FIG. 15. In an embodiment, one or more drill guide couplers 1116 comprise indentations in a superior wall 1120, and are configured to receive an equal number of protrusions in a drill guide. FIG. 11B shows an exemplary embodiment in which four drill guide couplers 1116 comprise four indentations arranged in a square pattern around a first opening 1112. In the exemplary embodiment, a drill guide with four protrusions is configured fit directly into the four drill guide couplers 1116 to properly align a screw to be placed through the drill guide and into the first opening 1112.

Figure 11C:
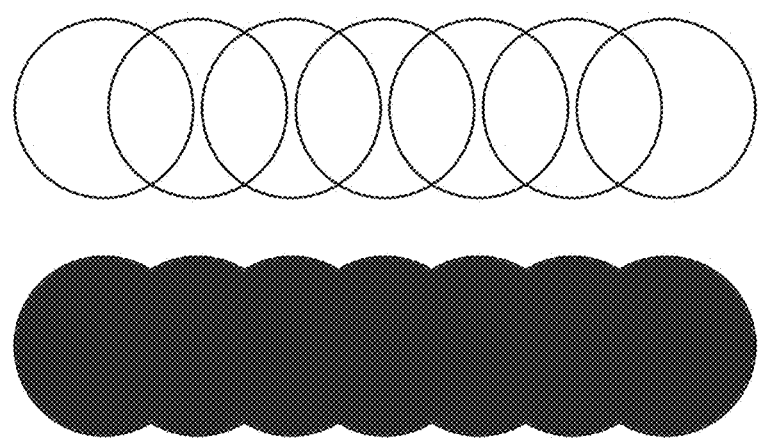
FIG. 11C shows a series of seven nested circles illustrating and embodiment of the configuration of the opening in the superior wall of the vertebral fixation device.

FIG. 11C shows a series of seven nested circles illustrating an embodiment of the configuration of the opening in the superior wall of the vertebral fixation device 1100. Nesting multiple holes within the superior wall of the vertebral fixation device 1100 will allow a screw that passes through the opening in the superior wall of the vertebral fixation device 1100 to catch or capture in one of the nested circles and lock the screw from movement along the slot. The number of nested holes that comprise an opening may vary from 2 to 9 and the spacing as a percentage of the circle radius may vary from 10% to 200%.

FIG. 12 shows a posterior view of an embodiment of a single level vertebral fixation system 1200. In an embodiment, a single level vertebral fixation system 1200 includes a left vertebral fixation device 1228, a right vertebral fixation device 1230 as described herein, two articulating couplers 1210, a horizontal rod 1224 and two small screws 1226. In an embodiment, a left vertebral fixation device 1228 and a right vertebral fixation device 1230 both comprise a lateral wall. In a left vertebral fixation device 1228 the lateral wall (not shown) is positioned on the left side of the device 1228 to securely fit around a left facet joint. In a right vertebral fixation device 1230 the lateral wall is positioned on the right side of the device 1230 to securely fit around a right facet joint. Horizontal rod 1224 may be coupled to the two articulating couplers 1210 and fixed in position with small screws 1226. In an embodiment, the articulating coupler 1210 comprises a saddle that is configured to securely couple with horizontal rod 1224 when a small screw 1226 is coupled together with the articulating coupler 1210. Fixing horizontal rod 1224 functions to prevent the articulating couplers 1210 from further articulating thus also fixing vertebral fixation devices 1228 and 1230 to each other. In an embodiment, vertebral fixation devices 1228 and 1230 are fixed to a left and a right cervical facet joint (as shown in, for example, FIG. 13) at the same spinal level with a screw (not shown) that passes through each vertebral fixation device 1228, 1230 and through the respective facet joints. The articulating couplers 1210 allow for variable positioning of the horizontal rod 1224 that is then fixed in position with placement of the small screws 1226. For example, a single level spinal fixation may fix two cervical vertebrae together by fixing together the right and left facet joints that join the two vertebrae together using the described single level vertebral fixation system.

FIG. 13 shows a posterior view of an embodiment of a multi-level vertebral fixation system. In an embodiment, a vertebral fixation system comprises four vertebral fixation devices 1330 as described herein, four articulating couplers 1310, four small screws, two vertical rods 1324, and an adjustable rod 1332. In the shown embodiment, two vertebral fixation devices 1330 are placed at two different spinal levels and fixed into right and left facet joints as described herein. In an embodiment, the articulating couplers 1310 of each of the four vertebral fixation devices 1330 is rotatable so that a vertical rod may, for example, be fixed in a vertical position fixing together, for example, two vertebral fixation devices 1330 on different levels of the same side of the spine. In an embodiment, the two vertical rods 1324 are further fixed together by an adjustable rod 1332. In an embodiment, an adjustable rod 1324 has a slideably adjustable length, wherein, the adjustable rod 1332 comprises components that are slideably coupled. In an embodiment, an adjustable rod 1332 is fixed to two vertical rods 1324 with screws or, alternatively, is clamped onto each vertical rod 1324 with a snap-on clamp. In an embodiment, the four vertebral fixation devices 1330 are fixed to a left and a right cervical facet joint (not shown) at two different spinal levels with a screw (not shown) that passes through each vertebral fixation device 1330 and through four respective facet joints. The articulating couplers 1310 allow for variable positioning of the vertical rods 1324, which are then fixed in position with placement of small screws that couple with the articulating couplers 1310. The two vertical rods 1324 may be further fixed together with, for example, an adjustable rod 1332 as shown in FIG. 13. In an exemplary embodiment of a multi-level fixation system 1300, a multi-level spinal fixation system 1300 may fix two levels of cervical vertebrae together by fixing together the right and left facet joints that join three vertebrae together.

FIG. 14 shows an embodiment of a multilevel vertebral fixation system coupled with the cervical spine. A left vertebral fixation device 1428a is positioned between a superior and inferior facet of a left facet joint as described herein. Two left vertebral fixation devices 1428a and 1428b may comprise a left lateral wall that both serves as a guide, and, in combination with two right vertebral fixation devices 1430a and 1430b (partially obscured), may provide lateral compression to the spine as described herein. Two right vertebral fixation devices 1430a and 1430b may comprise a right lateral wall, which both serves as a guide, and, in combination with two left vertebral fixation devices 1428a and 1428b, may provide lateral compression to the spine as described herein. The shown embodiment of the multilevel vertebral fixation system comprises four vertebral fixation devices 1428a, 1428b, 1430a, and 1430b, each positioned between a respective superior and inferior vertebral facet, four articulating couplers, an adjustable cross-connector 1432, and two vertical rods 1424a. An articulating coupler 1410 is coupled to a pin on a posterior wall of each of the four vertebral fixation devices 1428a, 1428b, 1430a, and 1430b. In an embodiment each of the four shown vertebral fixation devices 1428a, 1428b, 1430a, and 1430b may comprise an inferior wall that is inserted between a superior and an inferior vertebral facet. A space between the superior and inferior facets may exist naturally in certain patients or may require creation through known surgical techniques such as, for example, filing or rasping the facets. Once positioned, with its inferior wall between the superior and inferior facets, a screw may then be placed through a superior opening in each of the vertebral fixation devices 1428a, 1428b, 1430a, and 1430b at a selectable angle. In an embodiment, a respective superior facet is positioned within the recess of each of the vertebral fixation devices 1428a, 1428b, 1430a, and 1430b, and a screw passes through the first opening on each of the vertebral fixation devices 1428a, 1428b, 1430a, and 1430b, passes through the superior vertebral facet, passes through either a second or a third opening through an inferior wall of the vertebral fixation devices 1428a, 1428b, 1430a, and 1430b, and passes into the respective inferior facets, thus cinching the superior and inferior facets to the respective vertebral fixation devices 1428a, 1428b, 1430a, and 1430b. Four articulating couplers 1410 may be coupled to the pins of each of the four vertebral fixation devices 1428a, 1428b, 1430a, and 1430b either during a vertebral fixation procedure or before the procedure. In an embodiment, two articulating couplers on an ipsilateral side are positioned to receive and couple with a vertical rod 1424a. Thus, the vertical rod 1424a on the left side of the spine fixes the left sided vertebral fixation devices 1428a and 1428b to each other and a vertical rod 1424b on the right side of the spine fixes the right sided fixation devices 1430a and 1430b to each other. In an embodiment, while lateral compression is applied to the left 1428a, 1428b and right 1430a, 1430b vertebral fixation devices, an adjustable cross-connector 1432 is coupled with vertical rods 1424a and 1424b so that the adjustable cross-connector 1432 is held under tension and a lateral compressive force is applied to the spine through the left 1428a, 1428b and right 1430a, 1430b vertebral fixation devices.

FIG. 15 shows an inferior view of an embodiment of a drill guide 1500. In an embodiment, a drill guide 1500 reversibly couples with a vertebral fixation device as described herein. In an embodiment, drill guide 1500 has an opening 1536 that passes through an inferior wall of the drill guide 1500 and is configured to receive a screw (not shown). In an embodiment, drill guide 1500 comprises one or more protrusions 1534 (four are shown) that are configured to couple with a corresponding number of indentations on a vertebral fixation device. It should be understood that a number of ways of reversibly coupling a drill guide 1500 to a vertebral fixation device are suitable with the devices, systems, and methods described herein, including, for example, positioning one or more indentations on a drill guide 1500 that couple with one or more protrusions 1534 on a vertebral fixation device. For example, a drill guide coupling mechanism may comprise magnets. For example, in an embodiment, one or more protrusions 1534 and one or more indentations may be positioned on a drill guide and one or more protrusions 1534 and one or more indentations may be positioned on a superior wall of a vertebral fixation device.

FIG. 16 shows a superior view of an embodiment of a drill guide 1642 coupled with vertebral fixation device 1628. In an embodiment, a drill guide 1642 comprises first and second openings 1638, 1640 that go through a superior wall of the drill guide 1642 and connect to a single opening (not shown) that goes through an inferior wall of the drill guide and aligns with an opening through a superior wall on vertebral fixation device 1628. In an embodiment, when coupled with a vertebral fixation device, a drill guide 1642 accurately directs a screw to pass through the vertebral fixation device at one of two angles. For example, when a screw passes through first opening 1638 in the drill guide, it will be guided at a first angle through an opening in the superior wall of the vertebral fixation device, through a vertebral facet, and based on the first angle, through an opening 1646 in the inferior wall of the vertebral fixation device 1628. Alternatively, for example, when a screw passes through second opening 1640 in the drill guide, it will be guided at a second angle through an opening in the superior wall of the vertebral fixation device, through a vertebral facet, and based on the second angle, through an opening 1644 in the inferior wall of the vertebral fixation device 1628. In this exemplary embodiment of a drill guide 1642, when a user engages a vertebral fixation device 1628 with a vertebral facet he will be able to accurately select which one of two openings 1644, 1646 in an inferior wall of the vertebral fixation device 1628 to pass a screw through even though the user's view of the openings 1644 and 1646 will be blocked by the vertebral facet joint to which the vertebral fixation device 1628 is engaged. The drill guide 1642 comprises tracks having fixed angles that correspond to the angles of placement of a screw in either an opening 1644 or 1646, and a screw is guided on one of the two tracks by a user. It should be understood that just like a vertebral fixation device 1628 may comprise one or more openings on a superior and inferior wall, so to can a drill guide 1642 comprise one or more openings on a superior and inferior wall so that it can correspond to the openings on the vertebral fixation device 1628. Each opening on the superior surface of the vertebral guide corresponds to a track that guides a screw to at least one angle of delivery through a vertebral fixation device 1628.

Any of the embodiments described herein including any components of systems and devices described herein may comprise for example titanium, tantalum, stainless steel, chromium cobalt, or any other suitable metal or metal alloy.

While preferred embodiments of the presently described device have been shown and described herein, it will be obvious to those skilled in the art that such embodiments are provided by way of example only. Numerous embodiments, changes, and substitutions will now occur to those skilled in the art without departing from the device described herein. It should be understood that various alternatives to the embodiments of the device described herein may be employed.

What is claimed is:

1. A vertebral fixation method, comprising:
   coupling a first vertebral fixation device with a first superior facet of a right cervical facet joint, the first vertebral fixation device comprising:
   a first recess enclosed by a first superior wall, at least a portion of the first superior facet being positioned within the first recess;
   a first posterior wall;
   a first inferior wall configured to be positioned between the first superior facet and a first inferior facet of the right cervical facet joint; and
   a right lateral wall configured to contact the right cervical facet joint;
   coupling a second vertebral fixation device with a second superior facet of a left cervical facet joint, the second vertebral fixation device comprising:
   a second recess configured to be enclosed by a second superior wall, at least a portion of the second superior facet configured to be positioned within the second recess;
   a second posterior wall,
   a second inferior wall configured to be positioned between the second superior facet and a second inferior facet of the left cervical facet joint;
   a left lateral wall configured to contact the left cervical facet joint; and
   fixing a first rod to the first vertebral fixation device and to the second vertebral fixation device, so that a compressive force is applied to a first cervical vertebral facet joint and to a second cervical vertebral facet joint by the first vertebral fixation device and by the second vertebral fixation device, the compressive force applied to the right lateral wall and to the left lateral wall.

2. The method of claim 1, wherein the first rod is configured to fix to the first vertebral fixation device and the second vertebral fixation device by being coupled with a first articulating coupler of the first vertebral fixation device and a second articulating coupler of the second vertebral fixation device.

3. The method of claim 1, further comprising coupling a third vertebral fixation device with a third superior facet of a third cervical facet joint, wherein the third vertebral fixation device comprises a third recess configured to be enclosed by a third superior wall, a third posterior wall, and a third inferior wall, wherein at least a portion of the third superior facet is configured to be positioned within the third recess, and wherein the third inferior wall is configured to be positioned between the third superior facet and a third inferior facet of the third cervical facet joint.

4. The method of claim 3, further comprising:
   coupling a fourth vertebral fixation device with a fourth superior facet of a fourth cervical facet joint, wherein the fourth vertebral fixation device comprises a forth recess configured to be enclosed by a fourth superior wall, a fourth posterior wall, and a fourth inferior wall, wherein at least a portion of the fourth superior facet is configured to be positioned within the fourth recess, and wherein the fourth inferior wall is configured to be positioned between the fourth superior facet and a fourth inferior facet of the fourth cervical facet joint; and
   fixing a second rod to the third vertebral fixation device and to the fourth vertebral fixation device.

5. The method of claim 4, further comprising coupling the first rod to the second rod with an adjustable connector.

6. A vertebral fixation device, comprising:
   a body comprising:
   a superior wall, an inferior wall, a lateral wall, and a posterior wall, wherein the superior wall, the inferior wall, and the posterior wall are configured to join to form a recess within the body, wherein the recess is configured to receive a cervical vertebral facet within the recess of the body, and wherein the lateral wall is positioned over a lateral side of the body and is configured to enclose the recess within the body on only a single lateral side of the body;
   a first opening through the superior wall of the body; and
   a second opening through the inferior wall of the body, wherein the second opening is positioned on the inferior wall of the body, such that the second opening is configured to receive a screw passed through the first opening at a first angle.

7. The vertebral fixation device of claim 6, wherein the posterior wall of the body is coupled to a pin, wherein the pin is configured to couple to an articulating coupler configured to couple to a rod.

8. The vertebral fixation device of claim 7, wherein the pin comprises a spherical shape.

9. The vertebral fixation device of claim 7, wherein the articulating coupler comprises a tulip.

10. The vertebral fixation device of claim 6, further comprising a third opening through the inferior wall of the body, wherein the third opening is positioned on the inferior wall of the body, such that the third opening is configured to receive a rod or a screw passed through the first opening at a second angle.

11. The vertebral fixation device of claim 6, comprising a coupler on the superior wall configured to couple with a drill guide, wherein the coupler comprises an indentation in the superior wall of the body, wherein the indentation is configured to receive a protrusion on the drill guide.

12. The vertebral fixation device of claim 6, wherein the inferior wall is configured to be positioned between a superior facet and an inferior facet.

13. A vertebral fixation system, comprising:
a first body comprising:
a first superior wall, a first inferior wall, a first lateral wall, and a first posterior wall, wherein the first superior wall, the first inferior wall, and the first posterior wall are configured to join to form a recess within the first body, wherein the recess is configured to receive a first cervical vertebral facet within the recess of the first body, and wherein the first lateral wall is positioned over a right lateral side of the first body and is configured to enclose the recess within the first body on only a single lateral side of the first body;
a first opening through the first superior wall of the first body; and
a second opening through the first inferior wall of the first body, wherein the second opening is positioned on the first inferior wall of the first body, such that the second opening is configured to receive a first screw passed through the first opening at a first angle; and
a second body comprising:
a second superior wall, a second inferior wall, a second lateral wall, and a second posterior wall, wherein the second superior wall, the second inferior wall, and the second posterior wall are configured to join to form a second recess within the second body, wherein the second recess is configured to receive a second cervical vertebral facet within the second recess of the second body, and wherein the second lateral wall is positioned over a left lateral side of the second body and is configured to enclose the second recess within the second body on only a single lateral side of the second body;
a third opening through the second superior wall of the second body;
a fourth opening through the second inferior wall of the second body, wherein the fourth opening is positioned on the second inferior wall of the second body, such that the fourth opening is configured to receive a second screw passed through the third opening at a second angle; and
a first rod configured to couple to the first and the second bodies.

14. The vertebral fixation system of claim 13, wherein the first posterior wall or the second posterior wall of the first body or the second body is coupled to a first pin or a second pin, wherein the first pin or the second pin is configured to couple to a first articulating coupler of a second articulating coupler, wherein the first articulating coupler of the second articulating coupler is configured to couple to the first rod.

15. The vertebral fixation system of claim 14, wherein the first pin of the second pin is spherical shape.

16. The vertebral fixation system of claim 15, wherein the first articulating coupler of the second articulating coupler comprises a tulip.

17. The vertebral fixation system of claim 13, further comprising a coupler on the first superior wall and the second superior wall, wherein the coupler is configured to couple with a drill guide.

18. The vertebral fixation system of claim 17, wherein the coupler comprises an indentation in the first superior wall and the second superior wall of the first body and the second body, wherein the indentation is configured to receive a protrusion on the drill guide.

19. The vertebral fixation system of claim 13, wherein the first angle is the same as the second angle.

20. The vertebral fixation system of claim 13, further comprising:
a third body comprising:
a third superior wall, a third inferior wall, a third lateral wall, and a third posterior wall, wherein the third superior wall, the third inferior wall, and the third posterior wall are configured to join to form a third recess within the third body, wherein the third recess is configured to receive a third cervical vertebral facet within the third recess of the third body, and wherein the third lateral wall is positioned over a right lateral side of the third body and is configured to enclose the third recess within the third body;
a fifth opening through the third superior wall of the third body; and
a sixth opening through the third inferior wall of the third body, wherein the sixth opening is positioned on the third inferior wall of the third body, such that the sixth opening is configured to receive a third screw passed through the fifth opening at a third angle; and
a fourth body comprising:
a fourth superior wall, a fourth inferior wall, a fourth lateral wall, and a fourth posterior wall, wherein the fourth superior wall, the fourth inferior wall, and the fourth posterior wall are configured to join to form a fourth recess within the fourth body, wherein the recess is configured to receive a fourth cervical vertebral facet within the fourth recess of the fourth body, and wherein the fourth lateral wall is positioned over a left lateral side of the fourth body and is configured to enclose the fourth recess within the fourth body on only a single lateral side the fourth body;
a seventh opening through the fourth superior wall of the fourth body;
an eighth opening through the fourth inferior wall of the fourth body, wherein the seventh opening is positioned on the fourth inferior wall of the fourth body to receive a fourth screw passed through the seventh opening at a fourth angle; and
a second rod configured to couple to the third and fourth bodies.

21. The vertebral fixation system of claim 20, wherein the first rod is coupled to the second rod with an adjustable connector.

* * * * *